US011324821B2

(12) United States Patent
Martin et al.

(10) Patent No.: US 11,324,821 B2
(45) Date of Patent: May 10, 2022

(54) TRITERPENE SAPONIN ANALOGUES

(71) Applicant: ADJUVANCE TECHNOLOGIES, INC., Lincoln, NE (US)

(72) Inventors: J Tyler Martin, Roca, NE (US); Jeffrey Gardner, New York, NY (US)

(73) Assignee: ADJUVANCE TECHNOLOGIES, INC., Lincoln, NE (US)

(*) Notice: Subject to any disclaimer, the term of this patent is extended or adjusted under 35 U.S.C. 154(b) by 0 days.

(21) Appl. No.: 16/649,892

(22) PCT Filed: Oct. 15, 2018

(86) PCT No.: PCT/US2018/055828
§ 371 (c)(1),
(2) Date: Mar. 23, 2020

(87) PCT Pub. No.: WO2019/079160
PCT Pub. Date: Apr. 25, 2019

(65) Prior Publication Data

US 2020/0261571 A1 Aug. 20, 2020

Related U.S. Application Data

(60) Provisional application No. 62/572,857, filed on Oct. 16, 2017, provisional application No. 62/573,501, filed on Oct. 17, 2017.

(51) Int. Cl.
*A61K 39/39* (2006.01)
*A61K 39/00* (2006.01)
*A61K 31/704* (2006.01)

(52) U.S. Cl.
CPC ............ *A61K 39/39* (2013.01); *A61K 31/704* (2013.01); *A61K 39/00* (2013.01); *A61K 2039/55577* (2013.01)

(58) Field of Classification Search
None
See application file for complete search history.

(56) References Cited

U.S. PATENT DOCUMENTS 4,684,479 A 8/1987 D'Arrigo
5,215,680 A 6/1993 D'Arrigo
5,874,104 A 2/1999 Adler-Moore et al.
5,916,588 A 6/1999 Popescu et al.
5,965,156 A 10/1999 Proffitt et al.
6,043,094 A 3/2000 Martin et al.
6,056,973 A 5/2000 Allen et al.
6,080,725 A 6/2000 Marciani et al.
6,126,966 A 10/2000 Abra et al.
6,262,029 B1 7/2001 Press et al.
6,294,191 B1 9/2001 Meers et al.
6,316,024 B1 11/2001 Allen et al.
6,352,716 B1 3/2002 Janoff et al.
6,406,713 B1 6/2002 Janoff et al.
6,759,057 B1 7/2004 Weiner et al.
8,283,456 B2 10/2012 Gin et al.
8,889,842 B2 11/2014 Gin et al.
9,718,850 B2 * 8/2017 Gin ........................ A61P 31/22
10,906,926 B2 * 2/2021 Gin ........................ C07H 13/06
2009/0035360 A1 2/2009 Lemoine
2009/0047306 A1 2/2009 Nash et al.
2010/0272745 A1 10/2010 Lemoine et al.
2010/0322958 A1 12/2010 Bardotti et al.
2011/0104260 A1 5/2011 Hanon et al.
2011/0206758 A1 8/2011 Vandepapeliere
2012/0087976 A1 4/2012 Henderickx
2012/0164178 A1 6/2012 Ballou, Jr. et al.
2013/0011421 A1 1/2013 Gin et al.
2013/0309273 A1 11/2013 Hassett et al.
2014/0072622 A1 * 3/2014 Denoel ................ A61K 9/0019 424/450
2014/0228286 A1 8/2014 Luippold et al.
2015/0037374 A1 2/2015 Bazmorelli et al.
2015/0086585 A1 * 3/2015 Gin ........................ A61P 43/00 424/193.1
2017/0014507 A1 1/2017 Bazmorelli et al.
2018/0327436 A1 11/2018 Gin et al.
2020/0164065 A1 5/2020 Gardner et al.
2020/0239509 A1 7/2020 Gin et al.
2021/0002316 A1 1/2021 Gin et al.

FOREIGN PATENT DOCUMENTS

CL 2011003113 A1 8/2012
CL 2012000585 A1 9/2012
JP 2011-516566 A 5/2011
WO WO 2001/015727 A2 3/2001

(Continued)

OTHER PUBLICATIONS

Newman et al., Journal of Immunology, 1992, vol. 148, pp. 2357-2362. (Year: 1992).*
International Search Report, PCT/US2018/055828, dated Dec. 31, 2018, 2 pgs.
Adams et al., "Design and Synthesis of Potent Quillaja Saponin Vaccine Adjuvants", J Am Chem Soc. 1939(2010), vol. 132 (6), pp. 1-16.
Adams, "Synthesis of Saponin Immunoadjuvants", University of Illinois at Urbana-Champaign, Ph.D. Dissertation 2009 [retrieved on Jul. 18, 2018). Retrieved from the Internet: <URL: https://search.proquest.com/docview/304896057>. See Abstract, pp. 45-47.
Carcaboso et al., Potent, long lasting systematic antibody levels and mixed Th1/Th2 immune response after nasal immunization with malaria antigen loaded PLGA microparticles, Vaccine (2004), vol. 22, (11-12), pp. 1423-1432.

(Continued)

*Primary Examiner* — Traviss C McIntosh, III
(74) *Attorney, Agent, or Firm* — Paul D. Strain, Esq.; Strain & Strain PLLC

(57) ABSTRACT

The present application relates to triterpene glycoside saponin-derived adjuvants, syntheses thereof, and intermediates thereto. The application also provides pharmaceutical compositions comprising compounds of the present invention and methods of using said compounds or compositions in the treatment of and immunization for infectious diseases and cancers.

13 Claims, 10 Drawing Sheets

(56) References Cited

FOREIGN PATENT DOCUMENTS

| | | | |
|---|---|---|---|
| WO | WO 2006/094756 | A2 | 9/2006 |
| WO | WO 2009/080715 | A2 | 7/2009 |
| WO | WO 2009/126737 | A2 | 10/2009 |
| WO | WO 2010/142685 | A1 | 12/2010 |
| WO | WO 2011/027222 | A2 | 3/2011 |
| WO | WO 2015/184451 | A1 | 12/2015 |
| WO | WO 2017/079582 | A1 | 5/2017 |
| WO | WO 2017/106836 | A1 | 6/2017 |
| WO | WO 2018/191598 | A1 | 10/2018 |
| WO | WO 2018/200645 | A1 | 11/2018 |

OTHER PUBLICATIONS

Chea etal., "Synthesis and Preclinical Evaluation of QS-21 Variants Leading to Simplified Vaccine Adjuvants and Mechanistic Probes", J Am Chem Soc. vol. 134, No. 32 (2012), 26 pgs.

Evans et al., "QS-21 promotes an adjuvant effect allowing for reduced antigen dose during HIV-1 envelope subunit immunization in humans", Vaccine (2001), vol. 19, pp. 2080-2091.

Fernandez-Tejada et al., "Development of a minimal saponin vaccine adjuvant based on QS-21", Published in final edited form as: Nat Chem. vol. 6, No. 7 (2014), pp. 635-643.

Fernández-Tejada et al., "Development of Improved Vaccine Adjuvants Based on the Saponin Natural Product QS-21 through Chemical Synthesis", Accounts of Chemical Research (2016), vol. 49, pp. 1741-1756.

Fernández-Tejada et al., "Semisynthesis of Analogues of the Saponin Immunoadjuvant QS-21", Methods in Molecular Biology (2016), vol. 1494, pp. 45-71.

Fernández-Tejada et al., "Versatile Strategy for the Divergent Synthesis of Linear Oligosaccharide Domain Variants of Quillaja Saponin Vaccine Adjuvants", Chem Commun (2015), vol. 51 (73), pp. 13949-13952.

Fernandez-Tejada et al; "Design, synthesis, and immunologic evaluation of vaccine adjuvant conjugates based on QS-21 and tucaresol" Bioorganic & Medicinal Chemistry, vol. 22, No. 21 (2014), pp. 5917-5923.

Fernandez-Tejada et al; "Development of a Minimal Saponin Vaccine Adjuvant based on QS-21", Supplementary Information, Nature Chemistry, vol. 6 (2014), pp. S1-S135.

Gin et al., "Enhancing Immunogenicity of Cancer Vaccines: QS-21 as an Immune Adjuvant", Curr Drug ther. (2011), vol. 6 (3), pp. 207-212.

Kashala et al., "Safety, tolerability and immunogenicity of new formulations of the Plasmodium falciparum malaria peptide vaccine SPf66 combined with the immunological adjuvant QS-21", Vaccine (2002), vol. 20, pp. 2263-2277.

Kensil et al., "Separation and characterization of saponins with adjuvant activity from Quillaja saponaria Molina cortex", Journal of Immunology (1991), vol. 146 (2), pp. 431-437.

Kensil, "Saponins as Vaccine Adjuvants", Critical Reviews in Therapeutic Drug Carrier Systems (1996), vol. 13 (1&2), pp. 1-55.

Kim et al., "Comparison of the effect of different immunological adjuvants on the antibody and T-cell response to Immunization with MUC1-KLH and GD3-KLH conjugate cancer vaccines", Vaccine (2000), vol. 18, pp. 597-603.

Livingston et al., "Cancer vaccines targeting carbohydrate antigens", Human Vaccines (May-Jun. 2006), vol. 2 (3), pp. 137-143.

Newman et al., "Saponin adjuvant induction of ovalbumin-specific CD8+ cytotoxic T lymphocyte responses", Journal of Immunology (1992), vol. 148, pp. 2357-2362.

Ragupathi et al., "Natural and synthetic saponin adjuvant QS-21 for vaccines against cancer", Expert Rev Vaccines (2011), vol. 10 (4), pp. 463-470.

Ragupathi et al., "Preclinical Evaluation of the Synthetic Adjuvant SQS-21 and its Constituent Isomeric Saponins", Vaccine (2010), vol. 28 (26), pp. 4260-4267.

Sasaki et al., "Induction of systemic and mucosal immune responses to human immunodeficiency virus type 1 by a DNA vaccine formulated with QS-21 saponin adjuvant via intramuscular and intranasal routes", Journal of Virology (Jun. 1998), vol. 72 (6), pp. 4931-4939.

Soltysik et al., "Structure/function studies of QS-21 adjuvant: assessment of triterpene aldehyde and glucuronic acid roles in adjuvant function", Vaccine (1995), vol. 13 (15), pp. 1403-1410.

Van Setten et al., "Glycosyl compositions and structural characteristics of the potential immunoadjuvant active saponins in the Quillaja saponaria Mollina extract Quil A", Rapid Communications in Mass Spectrometry (1995), vol. 9, pp. 660-666.

Walkowicz et al., "Quillaja saponin variants with central glycosidic linkage modifications exhibit distinct conformations and adjuvant activities", Chem. Sci. (2016), vol. 7, pp. 2371-2380.

Wuts et al.; "Chapter 2: Protection for the Hydroxyl Group, Including 1,2- and 1,3-Diols", Greene's Protective Groups in Organic Synthesis, 4th Ed. (Dec. 31, 2006), 351 pgs.

Balsevich et al., "Analysis of bisdesmosidic saponins in *Saponaria vaccaria* L. by HPLC-PAD-MS: identification of new quillaic acid and gypsogenin 3-O-Trisaccharides." Phytochemical analysis, vol. 17, No. 6, pp. 414-423 (Oct. 18, 2006) (https://doi.org/10.1002/pca.943).

Guo et al., "Triterpenoid Saponins From Quillaja Saponaria" Phytochemistry, vol. 48, No. 1, pp. 175-180 (1998).

* cited by examiner

TRITERPENE SAPONIN ANALOGUES

INCORPORATION BY REFERENCE OF RELATED PATENT APPLICATIONS

This application is a National Stage of International Application No. PCT/US2018/055828, filed Oct. 15, 2018, which is based upon and claims the benefit of priority under 35 U.S.C. § 119(e) to U.S. Provisional Application No. 62/572,857, filed Oct. 16, 2017, and to U.S. Provisional Application No. 62/573,501, filed Oct. 17, 2017, the entire contents of all of which are incorporated herein by reference in their entirety.

GOVERNMENT SUPPORT

Some embodiments of the subject matter in this application were made with United States Government support under grant GRANT11540722 awarded by the National Institutes of Health. The United States Government has certain rights in the subject matter of this application.

FIELD OF THE INVENTION

The present application relates to triterpene glycoside saponin-derived adjuvants, syntheses thereof, and intermediates thereto. The application also provides pharmaceutical compositions comprising compounds of the present invention and methods of using said compounds or compositions in the treatment of infectious diseases.

BACKGROUND

Vaccines against infectious diseases continue to improve public health across the world. With increased knowledge of etiologic pathogens and necessary immune responses have come increasingly defined or targeted vaccines. Influenza, Hepatitis B, DTaP, HPV, pneumococcal and other widely used vaccines require use of the immunological adjuvant alum. However, alum, which was introduced over 80 years ago, is a poor adjuvant restricting the potency of some of these vaccines and requiring higher or more doses of others. Other, more modern adjuvant systems include TLR-based agonists. There is a need, however, for more potent adjuvant compounds, as such compounds reduce the amount of both adjuvant and vaccine antigen needed to generate the desired immune response. Such reduction can lead to significant vaccine savings, permitting lower-cost vaccination and more widespread availability.

SUMMARY

As discussed in Applicant's co-pending applications, PCT/US2018/027462, PCT/US2018/029314, PCT/US2018/029333, the contents of which are incorporated herein by reference in their entirety, novel synthetic and semi-synthetic saponin-based adjuvant systems show significant promise to advance the goals of achieving lower-cost vaccination and more widespread availability of vaccines. The present invention ecompasses the recognition that combinations of saponin-based adjuvant systems with TLR agonist-based systems achieve a surprising and significant synergistic immunostimulatory effect.

DETAILED DESCRIPTION OF CERTAIN EMBODIMENTS

Figure 1:
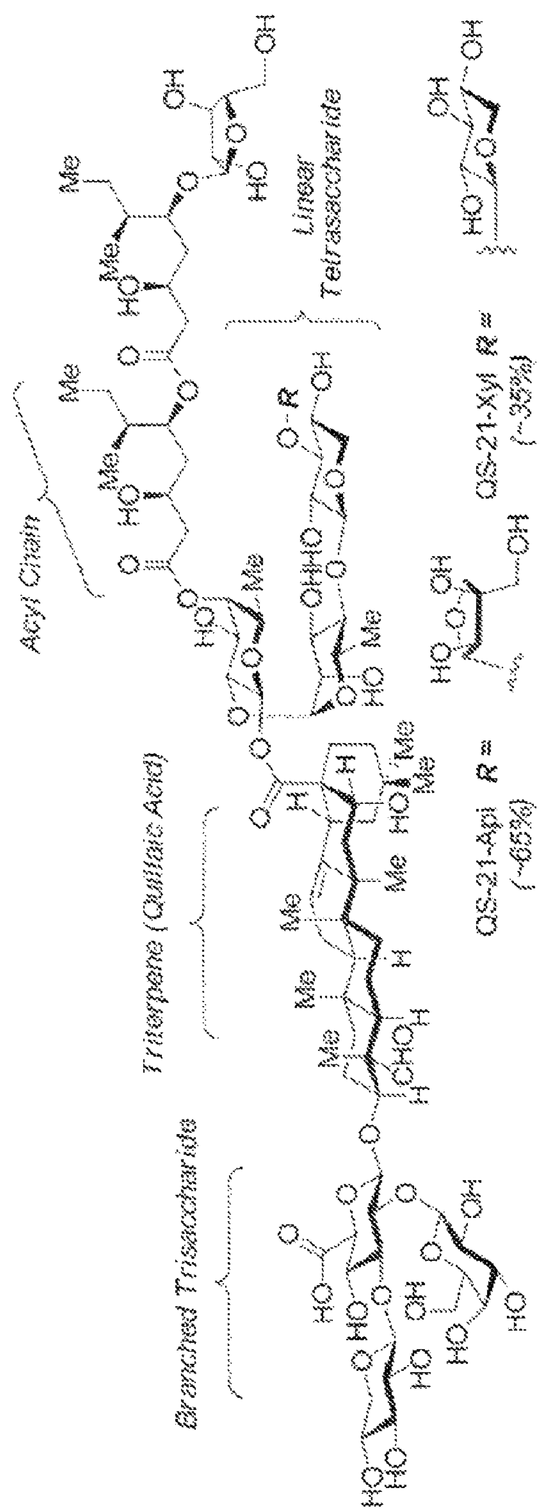
FIG. 1 depicts the chemical structure of QS-21-Api and QS-21-Xyl. Percentages correspond to the natural abundance of each isomer in isolated extracts of QS-21.
Figure 2:
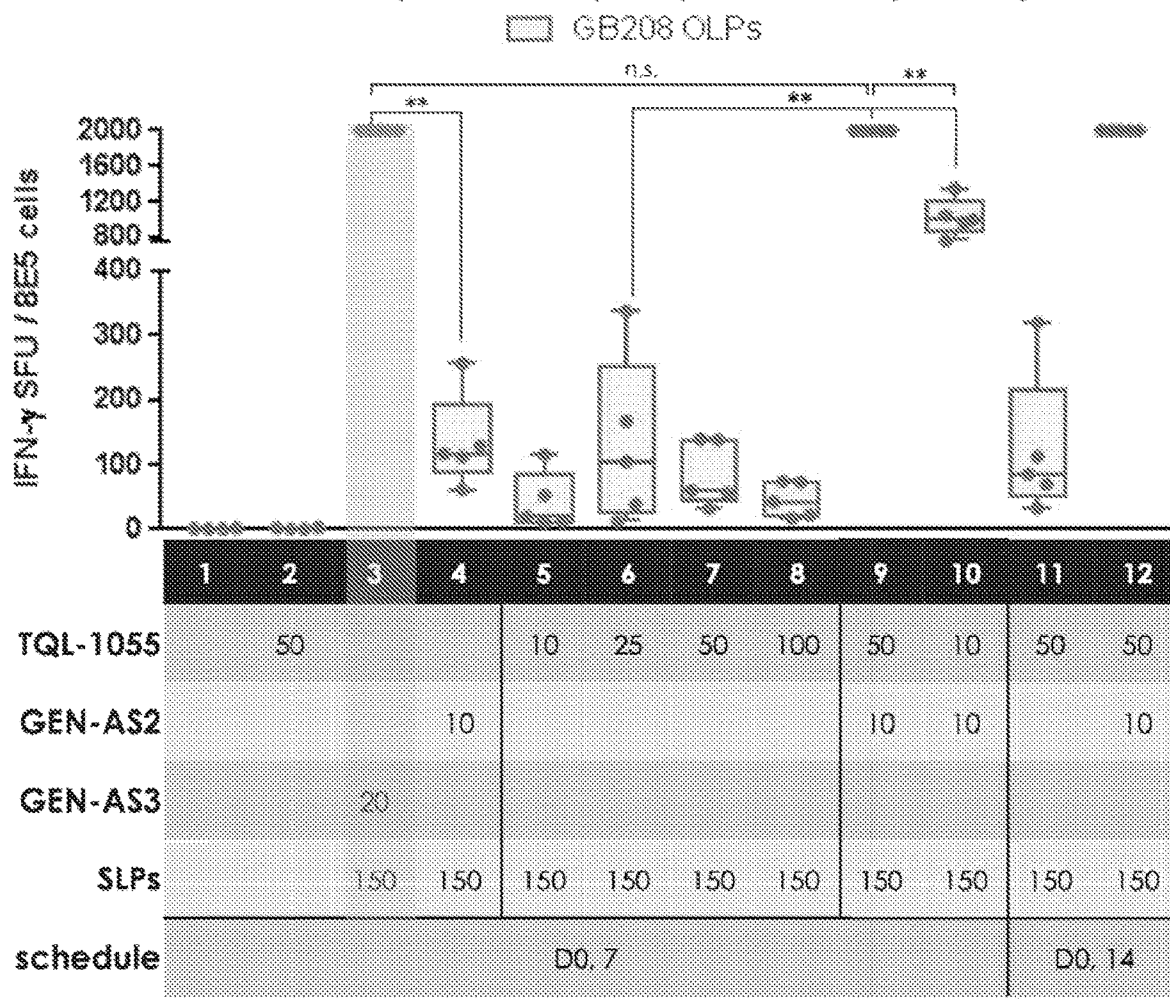
FIG. 2 depicts data showing ELISPOT assay results: GB208_1, _4, _8-specific INFγ responses in splenocytes for each group tested in Example 2.
Figure 3:
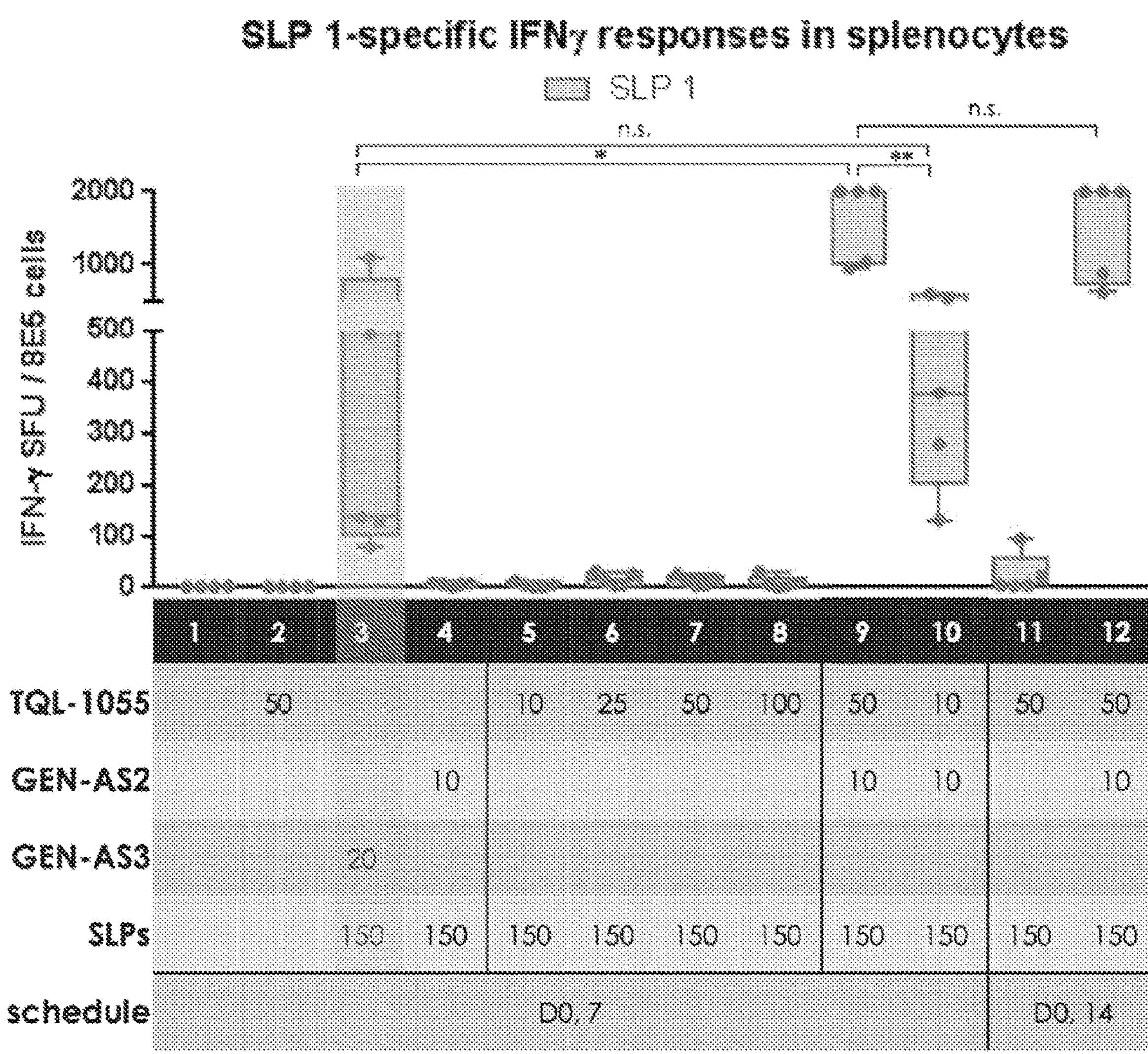
FIG. 3 depicts data showing ELISPOT assay results: GB208_1-specific INFγ responses in splenocytes for each group tested in Example 2.
Figure 4:
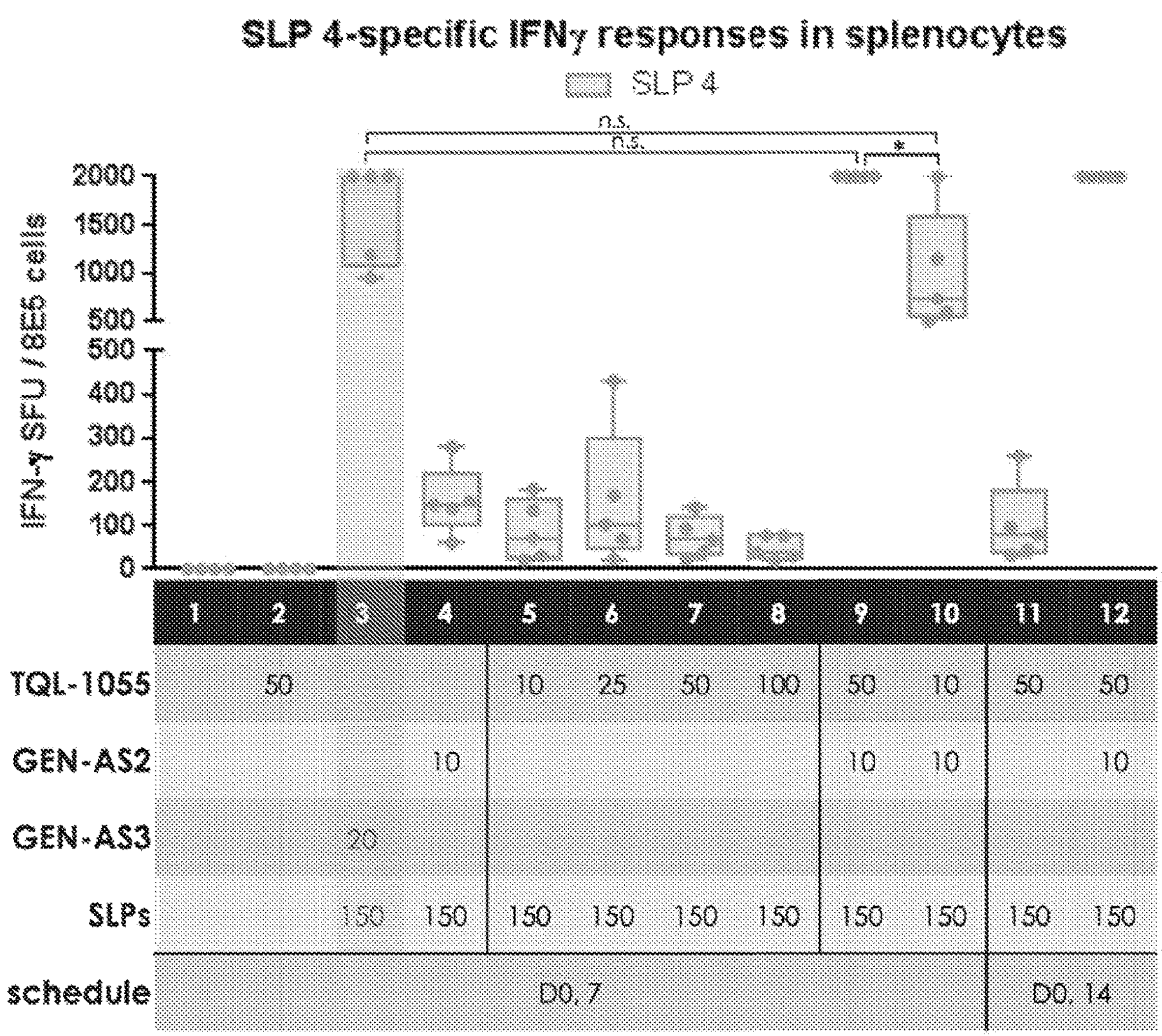
FIG. 4 depicts data showing ELISPOT assay results: GB208_4-specific INFγ responses in splenocytes for each group tested in Example 2.
Figure 5:
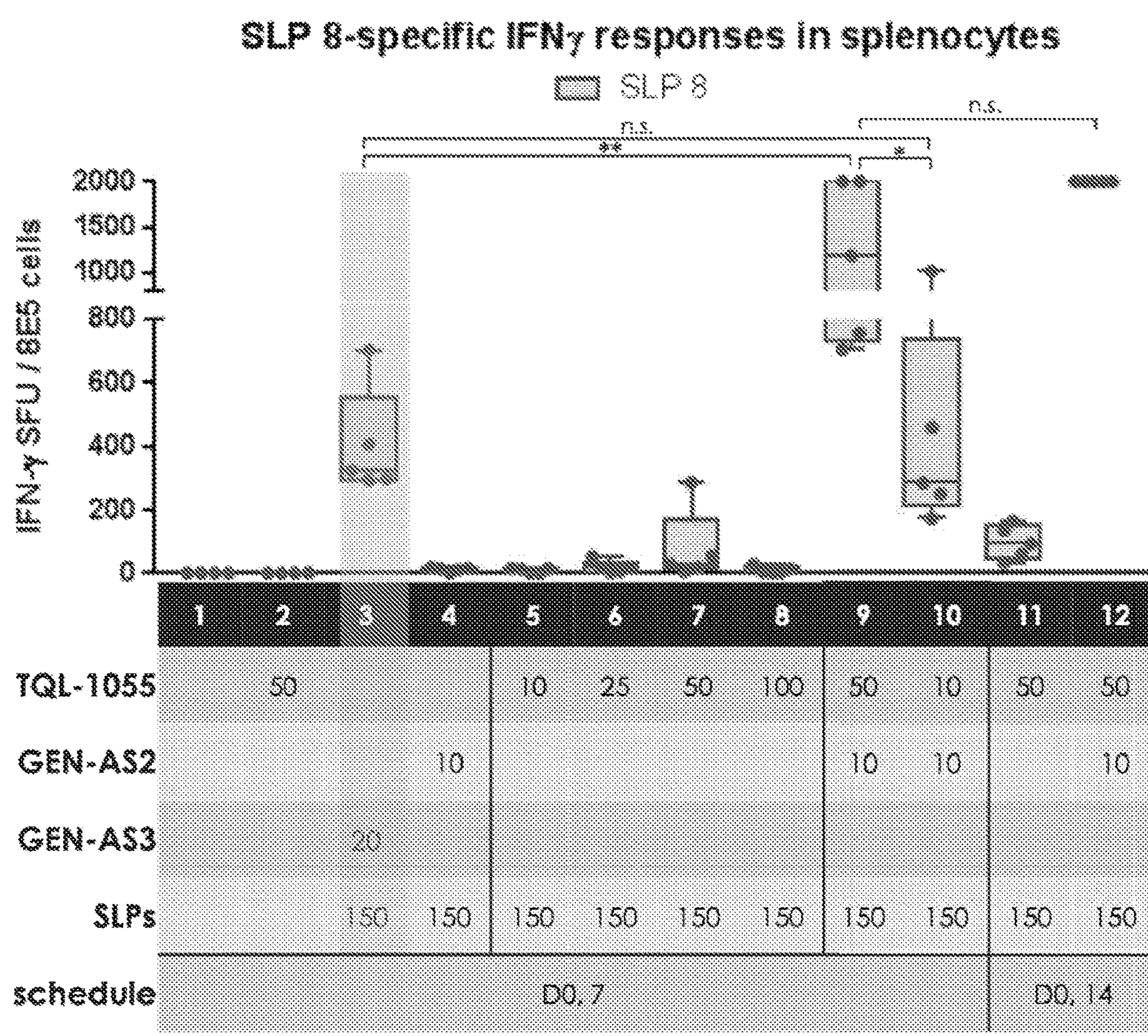
FIG. 5 depicts data showing ELISPOT assay results: GB208_8-specific INFγ responses in splenocytes for each group tested in Example 2.
Figure 6:
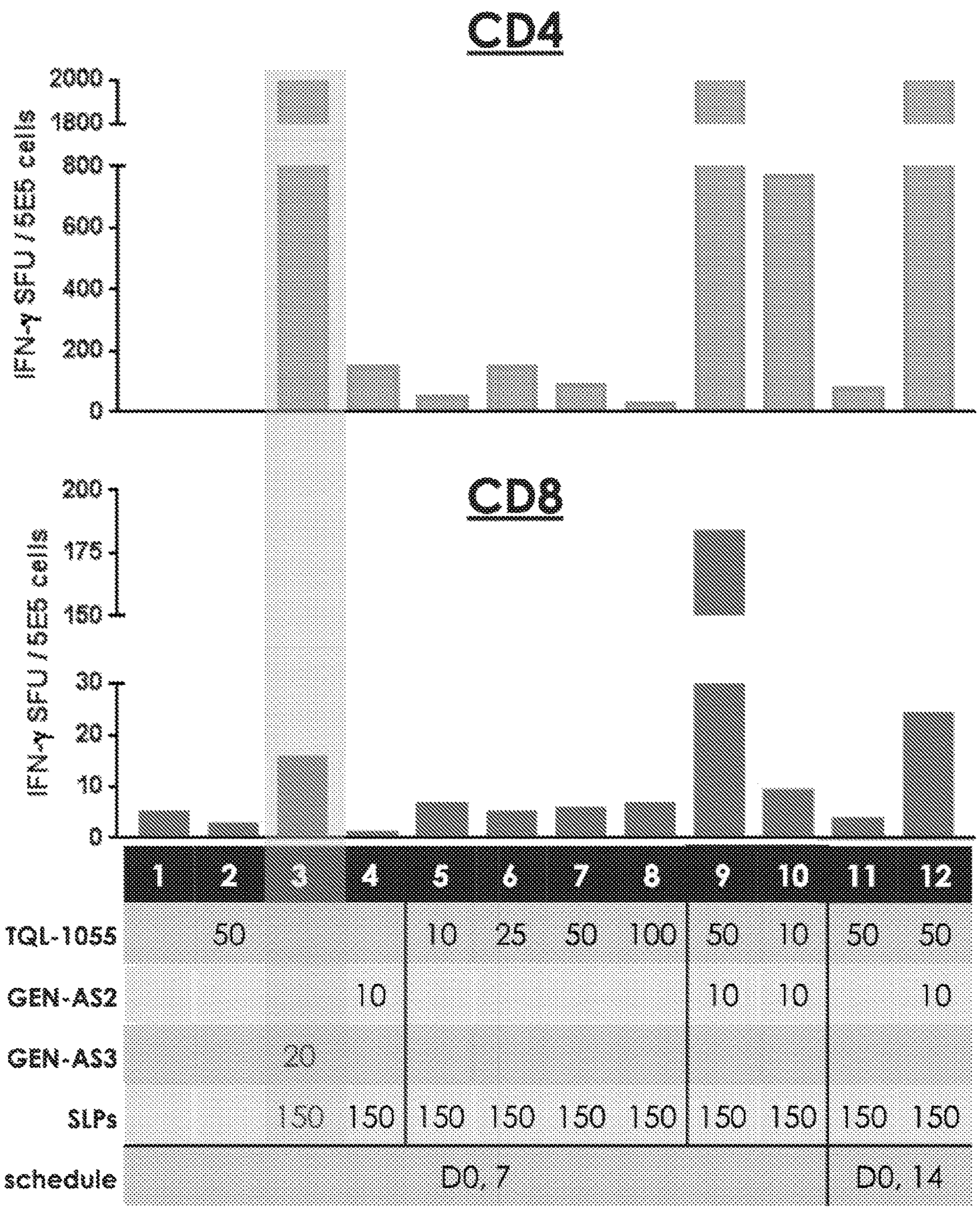
FIG. 6 depicts data showing ELISPOT assay results: sorted CD4 or CD8 responses to GB208_1, _4, _8 OLP for each group tested in Example 2.
Figure 7:
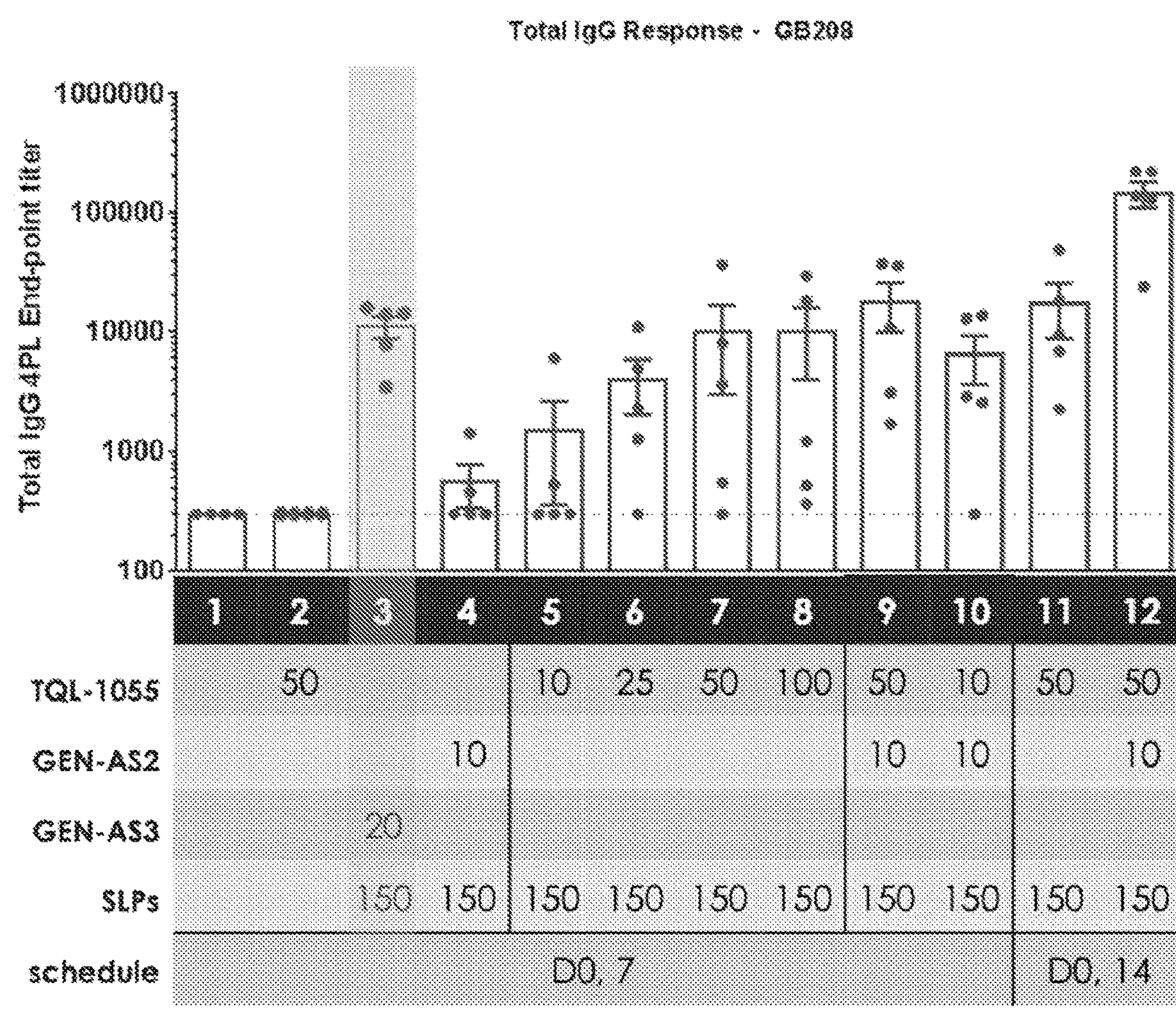
FIG. 7 depicts data showing enpoint titer data for total IgG response to GB208_1, _4, _8 for each group tested in Example 2.
Figure 8:
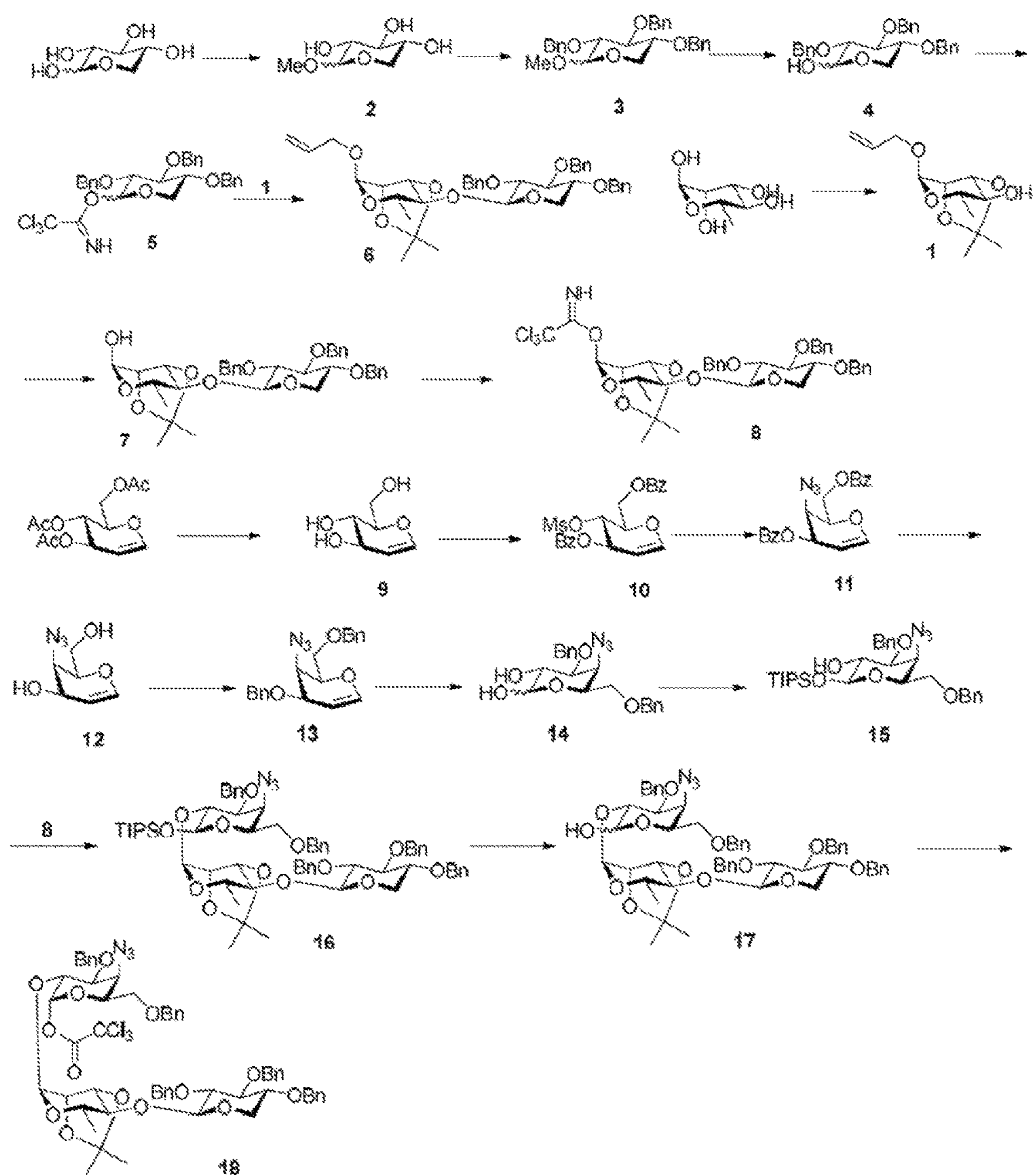
FIG. 8 depicts one synthetic route to obtain an intermediate used in the total synthesis of Compound I-4 (TiterQuil-1-0-5-5/TQL-1055).

The clinical success of anticancer, antiviral, and antimicrobial vaccines critically depends on the identification of, and access to, novel potent adjuvants with attenuated toxicity. In this context, specific fractions from extracts of the bark of *Quillaja saponaria* (QS) have proven to be exceedingly powerful adjuvants in immunotherapy. The QS-21 fraction (Kensil, C. R.; Patel, U.; Lennick, M.; Marciani, D. J. Immunol. 1991, 146, 431-437), comprising isomeric forms of a complex triterpene glycoside saponin (Soltysik, S.; Wu, J. Y.; Recchia, J.; Wheeler, D. A.; Newman, M. J.; Coughlin, R. T.; Kensil, C. R. Vaccine 1995, 13, 1403-1410; Kensil, C. R. Crit. Rev. Ther. Drug Carrier Syst. 1996, 13, 1-55), had previously been considered the most promising immuno-potentiator (Kim, S. K.; Ragupathi, G.; Musselli, C.; Choi, S. J.; Park, Y. S.; Livingston, P. O. Vaccine 2000, 18, 597-603) in several antitumor (melanoma, breast, small cell lung cancer, prostate) (Livingston, P. O.; Ragupathi, G. Hum. Vaccines 2006, 2, 137-143) and infectious-disease (HIV, malaria) vaccine therapies (Sasaki, S.; Sumino, K.; Hamajima, K.; Fukushima, J.; Ishii, N.; Kawamoto, S.; Mohri, H.; Kensil, C. R.; Okuda, K. J. Virol. 1998, 72, 4931-4939; Evans, T. G., et al. Vaccine 2001, 19, 2080-2091; Kashala, O., et al. Vaccine 2002, 20, 2263-2277; Carcaboso, A. M.; Hernandez, R. M.; Igartua, M.; Rosas, J. E.; Patarroyo, M. E.; Pedraz, J. L. Vaccine 2004, 22, 1423-1432).

However, the tolerated dose of QS-21 in cancer patients typically does not exceed 100-150 μg, above which significant local erythema and systemic flu-like symptoms arise. QS-21's inherent instability can lead to toxicities associated with its breakdown. It is also known that QS-21 is hemolytic, and this hemolytic activity had previously been hypothesized that at least some of QS-21's adjuvant activity was related to its hemolytic properties. Some of the various shortcomings of QS-21 have been partially addressed by formulation with emulsions (AS02 by GlaxoSmithKline (GSK) or liposomes (AS01, GSK)), however, these solutions are suboptimal and there remains a strong need for improved adjuvants that exhibit good adjuvant properties while maintaining a high degree of tolerability and/or reduced side-effects.

Now, surprisingly, the inventors of the present subject matter have found that compounds of the present application, which are in some embodiments synthetic analogues of QS-21 and other QS extraction fractions such as QS-7, possess significant stand-alone adjuvant activity as well as a high degree of tolerability and/or reduced side-effects. These new adjuvant compounds are more cost-effective to produce than natural QS-21, more stable, more efficacious, and less toxic for use in prophylactic and therapeutic vaccination programs. Some embodiments have no detectable toxicity in pharmacology/toxicology studies in mice at doses close to the likely 1000 mcg human dose. Some embodiments are surprisingly completely nonhemolytic while still retaining their adjuvant properties. This is surprising in part because it was initially thought that both QS-21 toxicity and potency were related to hemolysis and other cellular toxicity associated with QS-21. Some embodiments of the present application exhibit greater stability and less hemolytic activity by replacing the unstable ester linkage of the acyl chain in QS-21 with a very stable amide linkage, resulting in adjuvant active analogs of QS-21. Some embodiments also retain adjuvant activity despite having a simplified structure as compared to QS-21, resulting in higher synthetic yields and significantly reduced synthetic steps and cost of manufacture in comparison to synthetic QS-21.

The present application also provides efficient semi-synthetic methods of synthesizing the compounds of the present application, thereby significantly reducing the number of synthetic steps required to access this potent class of adjuvants.

The application also includes pharmaceutical compositions comprising the compounds of the present application together with an immunologically effective amount of an antigen associated with a bacterium or virus. Bacterium or viruses included in the subject matter of this application consist of those associated with influenza, Hepatitis B, pneumococcus, diphtheria, tetanus, pertussis, or Lyme disease including the closely related spirochetes of the genus *Borrelia* such as, *B. burgdorferi, B. garinii, B. afzelli*, and *B. japonica*.

The application also includes methods of vaccinating a human patient comprising administering an immunologically effective amount of a pharmaceutical compositions or of the compounds of the present application. The application also includes methods for increasing the immune response to a vaccine comprising administering an immunologically effective amount of a pharmaceutical compositions or of the compounds of the present application.

The present application also provides synergistic combinations of an adjuvant compound of the present application together with a TLR agonist-based system.

Compounds

Compounds of this invention include those described generally below, and are further illustrated by the classes, subclasses, and species disclosed herein. In some embodiments, provided compounds are analogs of naturally occurring triterpene glycoside saponins and intermediates thereto. For purposes of this invention, the chemical elements are identified in accordance with the Periodic Table of the Elements, CAS version, Handbook of Chemistry and Physics, 75th Ed. Additionally, general principles of organic chemistry are described in Organic Chemistry, Thomas Sorrell, University Science Books, Sausalito: 1999, and March's Advanced Organic Chemistry, 5th Ed., Ed.: Smith, M. B. and March, J., John Wiley & Sons, New York: 2001, the entire contents of which are hereby incorporated by reference.

Description of Exemplary Compounds

In some embodiments, provided compounds are analogs of *Quillaja saponins*. In some embodiments, provided compounds are prosapogenins. In certain embodiments, provided compounds are analogs of QS-7 and QS-21 and possess potent adjuvant activity.

In one aspect, the present application provides compounds of Formula I:

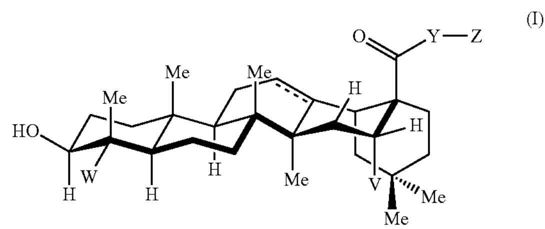

or a pharmaceutically acceptable salt thereof, wherein

⎓ is a single or double bond;

W is —CHO;

V is hydrogen or $OR^x$;

Y is $CH_2$, —O—, —NR—, or —NH—;

Z is hydrogen; a cyclic or acyclic, optionally substituted moiety selected from the group consisting of acyl, aliphatic, heteroaliphatic, aryl, arylalkyl, heteroacyl, and heteroaryl; or a carbohydrate domain having the structure:

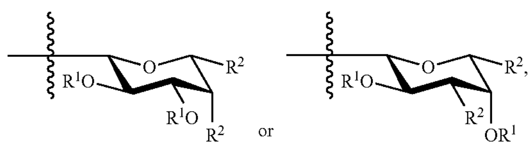

wherein each occurrence of $R^1$ is $R^x$ or a carbohydrate domain having the structure:

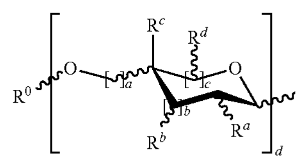

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is -T-$R^z$, —C(O)-T-$R^z$, —NH-T-$R^z$, —O-T-$R^z$, —S-T-$R^z$, —C(O)NH-T-$R^z$, C(O)O-T-$R^z$, C(O)S-T-$R^z$, C(O)NH-T-O-T-$R^z$, —O-T-$R^z$, -T-O-T-$R^z$, -T-S-T-$R^z$, or

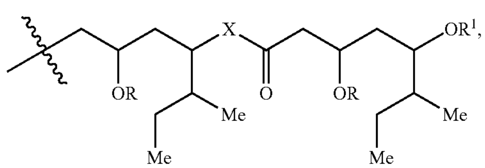

wherein

X is —O—, —NR—, or T-$R^z$;

T is a covalent bond or a bivalent $C_{1-26}$ saturated or unsaturated, straight or branched, aliphatic or heteroaliphatic chain; and $R^z$ is hydrogen, halogen, —OR, —$OR^x$, —$OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, carbamates, and carbonates;

each occurrence of R is independently hydrogen, an optionally substituted group selected from acyl, arylalkyl, 6-10-membered aryl, $C_{1-8}$ aliphatic, or $C_{1-6}$ heteroaliphatic having 1-2 heteroatoms independently selected from the group consisting of nitrogen, oxygen, and sulfur, or:

two R on the same nitrogen atom are taken with the nitrogen atom to form a 4-7-membered heterocyclic ring having 1-2 heteroatoms independently selected from the group consisting of nitrogen, oxygen, and sulfur.

In one aspect, the present application provides compounds of Formula II:

(II)

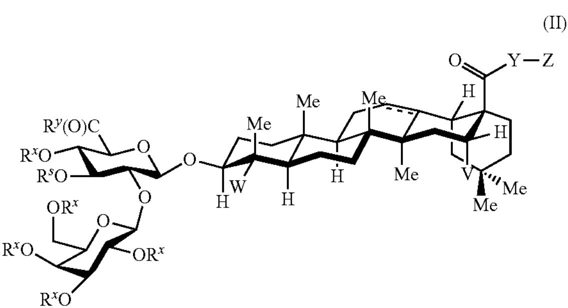

or a pharmaceutically acceptable salt thereof, wherein $\overline{\underline{\ \ }}$ is a single or double bond;

W is ME, —CHO, or

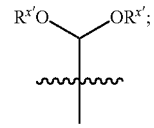

V is hydrogen or $OR^x$;

Y is $CH_2$, —O—, —NR—, or —NH—;

Z is hydrogen; a cyclic or acyclic, optionally substituted moiety selected from the group consisting of acyl, aliphatic, heteroaliphatic, aryl, arylalkyl, heteroacyl, and heteroaryl; or a carbohydrate domain having the structure:

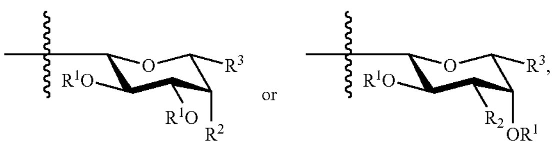

wherein each occurrence of $R^1$ is $R^x$ or a carbohydrate domain having the structure:

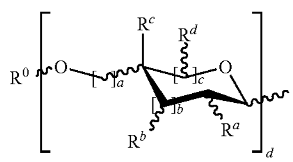

wherein:

each occurrence of a, b, and c is independently 0, 1, or 2;

d is an integer from 1-5, wherein each d bracketed structure may be the same or different; with the proviso that the d bracketed structure represents a furanose or a pyranose moiety, and the sum of b and c is 1 or 2;

$R^0$ is hydrogen; an oxygen protecting group selected from the group consisting of alkyl ethers, benzyl ethers, silyl ethers, acetals, ketals, esters, carbamates, and carbonates; or an optionally substituted moiety selected from the group consisting of acyl, $C_{1-10}$ aliphatic, $C_{1-6}$ heteroaliphatic, 6-10-membered aryl, arylalkyl, 5-10 membered heteroaryl having 1-4 heteroatoms independently selected from nitrogen, oxygen, or sulfur, 4-7 membered heterocyclyl having 1-2 heteroatoms independently selected from the group consisting of nitrogen, oxygen, and sulfur;

each occurrence of $R^a$, $R^b$, $R^c$, and $R^d$ is independently hydrogen, halogen, OH, OR, $OR^x$, $NR_2$, NHCOR, or an optionally substituted group selected from acyl, $C_{1-10}$ aliphatic, $C_{1-6}$ heteroaliphatic, 6-10-membered aryl, arylalkyl, 5-10-membered heteroaryl having 1-4 heteroatoms independently selected from nitrogen, oxygen, sulfur; 4-7-membered heterocyclyl having 1-2 heteroatoms independently selected from the group consisting of nitrogen, oxygen, and sulfur;

$R^2$ is hydrogen, halogen, OH, OR, $OC(O)R^4$, $OC(O)OR^4$, $OC(O)NHR^4$, $OC(O)NRR^4$, $OC(O)SR^4$, $NHC(O)R^4$, $NRC(O)R^4$, $NHC(O)OR^4$, $NHC(O)NHR^4$, $NHC(O)NRR^4$, $NHR^4$, $N(R^4)_2$, $NHR^4$, $NRR^4$, $N_3$, or an optionally substituted group selected from $C_{1-10}$ aliphatic, $C_{1-6}$ heteroaliphatic, 6-10-membered aryl, arylalkyl, 5-10 membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur;

$R^3$ is hydrogen, halogen, $CH_2OR^1$, or an optionally substituted group selected from the group consisting of acyl, $C_{1-10}$ aliphatic, $C_{1-6}$ heteroaliphatic, 6-10-membered aryl, arylalkyl, 5-10-membered heteroaryl having 1-4 heteroatoms independently selected from the group consisting of nitrogen, oxygen, and sulfur, 4-7-membered heterocyclyl having 1-2 heteroatoms independently selected from the group consisting of nitrogen, oxygen, and sulfur, $R^4$ is $-T-R^z$, $—C(O)-T-R^z$, $—NH-T-R^z$, $—O-T-R^z$, $—S-T-R^z$, $—C(O)NH-T-R^z$, $C(O)O-T-R^z$, $C(O)S-T-R^z$, $C(O)NH-T-O-T-R^z$, $—O-T-R^z$, $-T-O-T-R^z$, $-T-S-T-R^z$, or

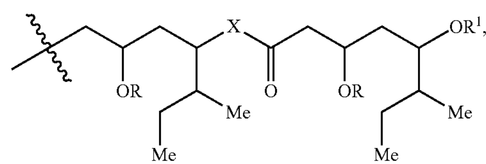

wherein

X is —O—, —NR—, or $T-R^z$;

T is a covalent bond or a bivalent $C_{1-26}$ saturated or unsaturated, straight or branched, aliphatic or heteroaliphatic chain; and $R^z$ is hydrogen, halogen, —OR, $—OR^x$, $—OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur;

each occurrence of $R^x$ is independently hydrogen or an oxygen protecting group selected from the group consisting of alkyl ethers, benzyl ethers, silyl ethers, acetals, ketals, esters, carbamates, and carbonates;

$R^y$ is —OH, —OR, or a carboxyl protecting group selected from the group consisting of ester, amides, and hydrazides;

$R^s$ is

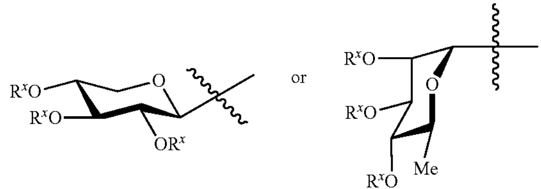

each occurrence of $R^{x'}$ is independently an optionally substituted group selected from 6-10-membered aryl, $C_{1-6}$ aliphatic, or $C_{1-6}$ heteroaliphatic having 1-2 heteroatoms independently selected from the group consisting of nitrogen, oxygen, and sulfur; or:

two $R^{x'}$ are taken together to form a 5-7-membered heterocyclic ring having 1-2 heteroatoms independently selected from the group consisting of nitrogen, oxygen, and sulfur;

each occurrence of R is independently hydrogen, an optionally substituted group selected from acyl, arylalkyl, 6-10-membered aryl, $C_{1-6}$ aliphatic, or $C_{1-6}$ heteroaliphatic having 1-2 heteroatoms independently selected from the group consisting of nitrogen, oxygen, and sulfur, or:

two R on the same nitrogen atom are taken with the nitrogen atom to form a 4-7-membered heterocyclic ring having 1-2 heteroatoms independently selected from the group consisting of nitrogen, oxygen, and sulfur.

In one aspect, the present application provides compounds of Formula I:

(I)

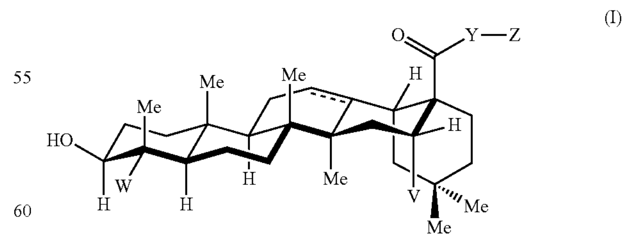

or a pharmaceutically acceptable salt thereof, wherein

⎓ is a single or double bond;

W is —CHO;

V is —OH;

Y is —O—;

wherein Z is a carbohydrate domain having the structure:

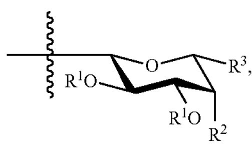

wherein:

$R^1$ is independently H or

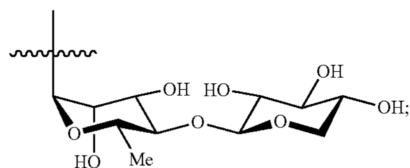

$R^2$ is $NHR^4$;

$R^3$ is $CH_2OH$; and $R^4$ is -T-$R^z$, —C(O)-T-$R^z$, —NH-T-$R^z$, —O-T-$R^z$, —S-T-$R^z$, —C(O)NH-T-$R^z$, C(O)O-T-$R^z$, C(O)S-T-$R^z$, C(O)NH-T-O-T-$R^z$, —O-T-$R^z$, -T-O-T-$R^z$, -T-S-T-$R^z$, or

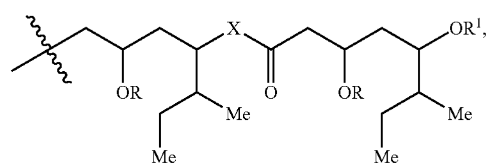

wherein:

X is —O—, —NR—, or T-$R^z$;

T is a covalent bond or a bivalent $C_{1-26}$ saturated or unsaturated, straight or branched, aliphatic or heteroaliphatic chain; and $R^z$ is hydrogen, halogen, —OR, —$OR^x$, —$OR^1$, —SR, $NR_2$, —C(O)OR, —C(O)R, —NHC(O)R, —NHC(O)OR, NC(O)OR, or an optionally substituted group selected from acyl, arylalkyl, heteroarylalkyl, $C_{1-6}$ aliphatic, 6-10-membered aryl, 5-10-membered heteroaryl having 1-4 heteroatoms independently selected from nitrogen, oxygen, or sulfur, 4-7-membered heterocyclyl having 1-2 heteroatoms independently selected from the group consisting of nitrogen, oxygen, and sulfur.

It will be appreciated by one of ordinary skill in the art that the compounds of the present application include but are not necessarily limited to those compounds encompassed in the genus definitions set forth as part of the present section. The compounds encompassed by this application include at least all of the compounds disclosed in the entire specification as a whole, including all individual species within each genus.

In certain embodiments, V is $OR^x$. In certain embodiments V is OH. In certain embodiments, V is H.

In certain embodiments, Y is —O—. In certain embodiments, Y is —NH—. In certain embodiments, Y is —NR—. In certain embodiments, Y is $CH_2$.

In certain embodiments, Z is hydrogen. In certain embodiments, Z is a cyclic or acyclic, optionally substituted moiety. In certain embodiments, Z is an acyl. In certain embodiments, Z is an aliphatic. In certain embodiments, Z is a heteroaliphatic. In certain embodiments, Z is aryl. In certain embodiments Z is arylalkyl. In certain embodiments, Z is heteroacyl. In certain embodiments, Z is heteroaryl. In certain embodiments, Z is a carbohydrate domain having the structure:

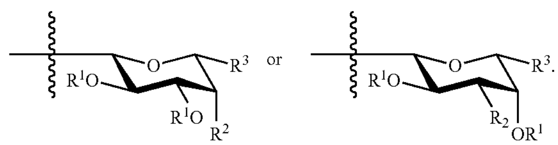

In some embodiments Z is a carbohydrate domain having the structure:

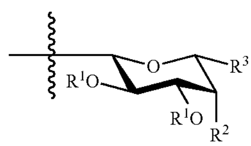

wherein:

$R^1$ is independently H or

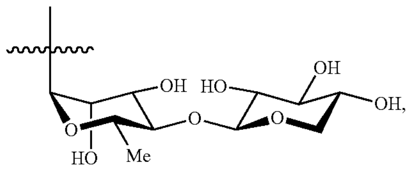

$R^2$ is $NHR^4$, $R^3$ is $CH_2OH$, and $R^4$ is selected from:

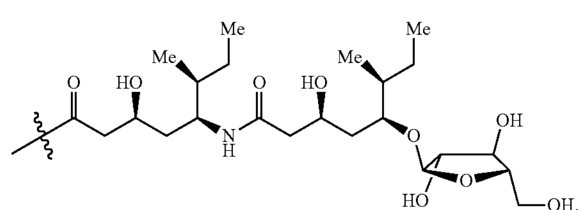

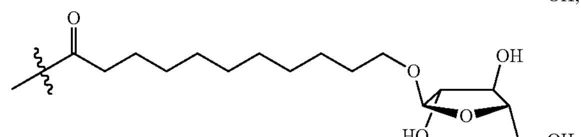

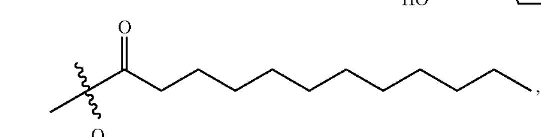

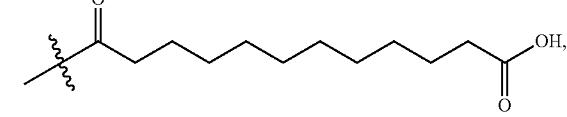

-continued

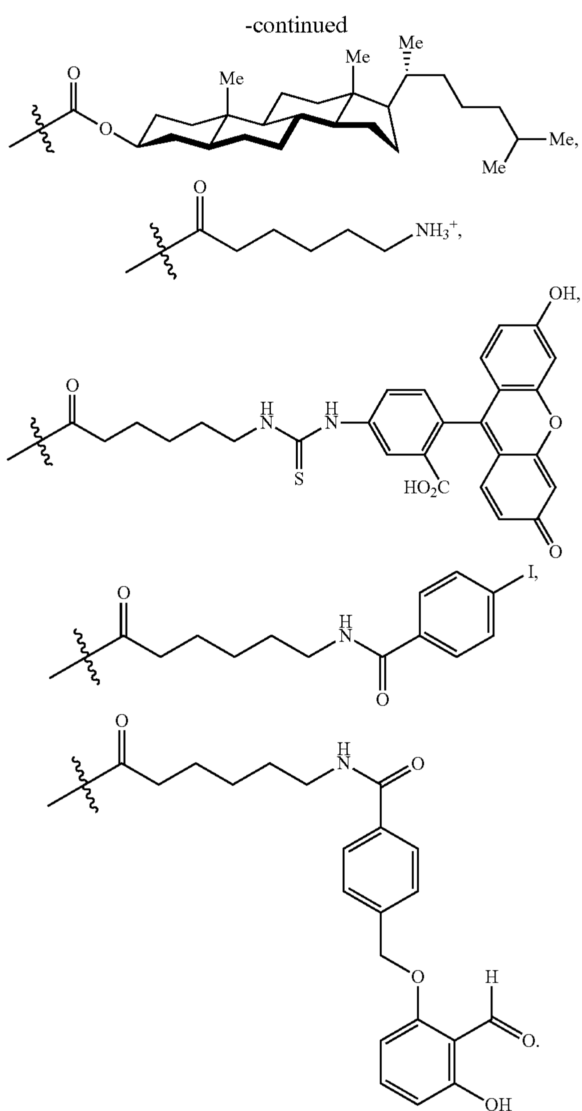

In some embodiments, $R^1$ is $R^x$. In other embodiments, $R^1$ a carbohydrate domain having the structure:

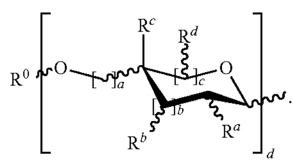

In some aspects, each occurrence of a, b, and c is independently 0, 1, or 2. In some embodiments, d is an integer from 1-5. In some embodiments, each d bracketed structure may be the same. In some embodiments, each d bracketed structure may be different. In some embodiments, the d bracketed structure represents a furanose or a pyranose moiety. In some embodiments, and the sum of b and c is 1 or 2.

In some embodiments, $R^0$ is hydrogen. In some embodiments, $R^0$ is an oxygen protecting group selected from the group. In some embodiments, $R^0$ is an alkyl ether. In some embodiments, $R^0$ is a benzyl ether. In some embodiments, $R^0$ is a silyl ether. In some embodiments, $R^0$ is an acetal. In some embodiments, $R^0$ is ketal. In some embodiments, $R^0$ is an ester. In some embodiments, $R^0$ is a carbamate. In some embodiments, $R^0$ is a carbonate. In some embodiments, $R^0$ is an optionally substituted moiety. In some embodiments, $R^0$ is an acyl. In some embodiments, $R^0$ is a $C_{1-10}$ aliphatic. In some embodiments, $R^0$ is a $C_{1-6}$ heteroaliphatic. In some embodiments, $R^0$ is a 6-10-membered aryl. In some embodiments, $R^0$ is a arylalkyl. In some embodiments, $R^0$ is a 5-10 membered heteroaryl having 1-4 heteroatoms independently selected from nitrogen, oxygen, or sulfur. In some embodiments, $R^0$ is a 4-7 membered heterocyclyl having 1-2 heteroatoms independently selected from the group consisting of nitrogen, oxygen, and sulfur.

In some embodiments, $R^a$ is hydrogen. In some embodiments, $R^a$ is a halogen. In some embodiments, $R^a$ is OH. In some embodiments, $R^a$ is OR. In some embodiments, $R^a$ is $OR^x$. In some embodiments, $R^a$ is $NR_2$. In some embodiments, $R^a$ is NHCOR. In some embodiments, $R^a$ an acyl. In some embodiments, $R^a$ is $C_{1-10}$ aliphatic. In some embodiments, $R^a$ is $C_{1-6}$ heteroaliphatic. In some embodiments, $R^a$ is 6-10-membered aryl. In some embodiments, $R^a$ is arylalkyl. In some embodiments, $R^a$ is 5-10-membered heteroaryl having 1-4 heteroatoms independently selected from nitrogen, oxygen, sulfur. In some embodiments, $R^a$ is 4-7-membered heterocyclyl having 1-2 heteroatoms independently selected from the group consisting of nitrogen, oxygen, and sulfur.

In some embodiments, $R^b$ is hydrogen. In some embodiments, $R^b$ is a halogen. In some embodiments, $R^b$ is OH. In some embodiments, $R^b$ is OR. In some embodiments, $R^b$ is $OR^x$. In some embodiments, $R^b$ is $NR_2$. In some embodiments, $R^b$ is NHCOR. In some embodiments, $R^b$ an acyl. In some embodiments, $R^b$ is $C_{1-10}$ aliphatic. In some embodiments, $R^b$ is $C_{1-6}$ heteroaliphatic. In some embodiments, $R^b$ is 6-10-membered aryl. In some embodiments, $R^b$ is arylalkyl. In some embodiments, $R^b$ is 5-10-membered heteroaryl having 1-4 heteroatoms independently selected from nitrogen, oxygen, sulfur. In some embodiments, $R^b$ is 4-7-membered heterocyclyl having 1-2 heteroatoms independently selected from the group consisting of nitrogen, oxygen, and sulfur.

In some embodiments, $R^b$ is hydrogen. In some embodiments, $R^b$ is a halogen. In some embodiments, $R^b$ is OH. In some embodiments, $R^b$ is OR. In some embodiments, $R^b$ is $OR^x$. In some embodiments, $R^b$ is $NR_2$. In some embodiments, $R^b$ is NHCOR. In some embodiments, $R^b$ an acyl. In some embodiments, $R^b$ is $C_{1-10}$ aliphatic. In some embodiments, $R^b$ is $C_{1-6}$ heteroaliphatic. In some embodiments, $R^b$ is 6-10-membered aryl. In some embodiments, $R^b$ is arylalkyl. In some embodiments, $R^b$ is 5-10-membered heteroaryl having 1-4 heteroatoms independently selected from nitrogen, oxygen, sulfur. In some embodiments, $R^b$ is 4-7-membered heterocyclyl having 1-2 heteroatoms independently selected from the group consisting of nitrogen, oxygen, and sulfur.

In some embodiments, $R^c$ is hydrogen. In some embodiments, $R^0$ is a halogen. In some embodiments, $R^c$ is OH. In some embodiments, $R^0$ is OR. In some embodiments, $R^c$ is $OR^x$. In some embodiments, $R^c$ is $NR_2$. In some embodiments, $R^c$ is NHCOR. In some embodiments, $R^c$ an acyl. In some embodiments, $R^c$ is $C_{1-10}$ aliphatic. In some embodiments, $R^c$ is $C_{1-6}$ heteroaliphatic. In some embodiments, $R^c$ is 6-10-membered aryl. In some embodiments, $R^c$ is arylalkyl. In some embodiments, $R^c$ is 5-10-membered heteroaryl having 1-4 heteroatoms independently selected from nitrogen, oxygen, sulfur. In some embodiments, $R^c$ is 4-7-membered heterocyclyl having 1-2 heteroatoms independently selected from the group consisting of nitrogen, oxygen, and sulfur.

In some embodiments, $R^d$ is hydrogen. In some embodiments, $R^d$ is a halogen. In some embodiments, $R^d$ is OH. In some embodiments, $R^d$ is OR. In some embodiments, $R^d$ is $OR^x$. In some embodiments, $R^d$ is $NR_2$. In some embodiments, $R^d$ is NHCOR. In some embodiments, $R^d$ an acyl. In some embodiments, $R^d$ is $C_{1-10}$ aliphatic. In some embodiments, $R^d$ is $C_{1-6}$ heteroaliphatic. In some embodiments, $R^d$ is 6-10-membered aryl. In some embodiments, $R^d$ is arylalkyl. In some embodiments, $R^d$ is 5-10-membered heteroaryl having 1-4 heteroatoms independently selected from nitrogen, oxygen, sulfur. In some embodiments, $R^d$ is 4-7-membered heterocyclyl having 1-2 heteroatoms independently selected from the group consisting of nitrogen, oxygen, and sulfur.

In some embodiments, $R^2$ is hydrogen. In some embodiments, $R^2$ is a halogen. In some embodiments, $R^2$ is OH. In some embodiments, $R^2$ is OR. In some embodiments, $R^2$ is $OC(O)R^4$. In some embodiments, $R^2$ is $OC(O)OR^4$. In some embodiments, $R^2$ is $OC(O)NHR^4$. In some embodiments, $R^2$ is $OC(O)NRR^4$. In some embodiments, $R^2$ is $OC(O)SR^4$. In some embodiments, $R^2$ is $NHC(O)R^4$. In some embodiments, $R^2$ is $NRC(O)R^4$. In some embodiments, $R^2$ is $NHC(O)OR^4$. In some embodiments, $R^2$ is $NHC(O)NHR^4$. In some embodiments, $R^2$ is $NHC(O)NRR^4$. In some embodiments, $R^2$ is $NHR^4$. In some embodiments, $R^2$ is $N(R^4)_2$. In some embodiments, $R^2$ is $NHR^4$. In some embodiments, $R^2$ is $NRR^4$. In some embodiments, $R^2$ is $N_3$. In some embodiments, $R^2$ is $C_{1-10}$ aliphatic. In some embodiments, $R^2$ is $C_{1-6}$ heteroaliphatic. In some embodiments, $R^2$ is 6-10-membered aryl. In some embodiments, $R^2$ is arylalkyl. In some embodiments, $R^2$ is 5-10 membered heteroaryl having 1-4 heteroatoms independently selected from the group consisting of nitrogen, oxygen, and sulfur. In some embodiments, $R^2$ is 4-7-membered heterocyclyl having 1-2 heteroatoms independently selected from the group consisting of nitrogen, oxygen, and sulfur.

In some embodiments, $R^3$ is hydrogen. In some embodiments, $R^3$ is a halogen. In some embodiments, $R^3$ is $CH_2OR^1$. In some embodiments, $R^3$ is an acyl. In some embodiments, $R^3$ is $C_{1-10}$ aliphatic. In some embodiments, $R^3$ is $C_{1-6}$ heteroaliphatic. In some embodiments, $R^3$ is 6-10-membered aryl. In some embodiments, $R^3$ is arylalkyl. In some embodiments, $R^3$ is 5-10-membered heteroaryl having 1-4 heteroatoms independently selected from the group consisting of nitrogen, oxygen, and sulfur. In some embodiments, $R^3$ is 4-7-membered heterocyclyl having 1-2 heteroatoms independently selected from the group consisting of nitrogen, oxygen, and sulfur.

In some embodiments, $R^4$ is $-T-R^z$. In some embodiments, $R^4$ is $—C(O)-T-R^z$. In some embodiments, $R^4$ is $—NH-T-R^z$. In some embodiments, $R^4$ is $—O-T-R^z$. In some embodiments, $R^4$ is $—S-T-R^z$. In some embodiments, $R^4$ is $—C(O)NH-T-R^z$. In some embodiments, $R^4$ is $C(O)O-T-R^z$. In some embodiments, $R^4$ is $C(O)S-T-R^z$. In some embodiments, $R^4$ is $C(O)NH-T-O-T-R^z$. In some embodiments, $R^4$ is $—O-T-R^z$. In some embodiments, $R^4$ is $-T-O-T-R^z$. In some embodiments $R^4$ is $-T-S-T-R^z$. In some embodiments, $R^4$ is

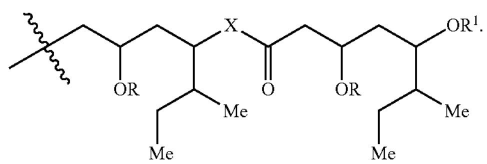

In some embodiments, X is —O—. In some embodiments, X is —NR—. In some embodiments, X is $T-R^z$.

In some embodiments, T is a covalent bond or a bivalent $C_{1-26}$ saturated or unsaturated, straight or branched, aliphatic or heteroaliphatic chain.

In some embodiments, $R^z$ is hydrogen. In some embodiments, $R^z$ is a halogen. In some embodiments, $R^z$ is —OR. In some embodiments, $R^z$ is $—OR^x$. In some embodiments, $R^z$ is $—OR^1$. In some embodiments, $R^z$ is $—OR^{1'}$. In some embodiments, $R^z$ is —SR. In some embodiments, $R^z$ is $NR_2$. In some embodiments, $R^z$ is —C(O)OR. In some embodiments, $R^z$ is —C(O)R. In some embodiments, $R^z$ is —NHC(O)R. In some embodiments, $R^z$ is —NHC(O)OR. In some embodiments, $R^z$ is NC(O)OR. In some embodiments, $R^z$ is an acyl. In some embodiments, $R^z$ is arylalkyl. In some embodiments, $R^z$ is heteroarylalkyl. In some embodiments, $R^z$ is $C_{1-6}$ aliphatic. In some embodiments, $R^z$ is 6-10-membered aryl. In some embodiments, $R^z$ is 5-10-membered heteroaryl having 1-4 heteroatoms independently selected from nitrogen, oxygen, or sulfur. In some embodiments, $R^z$ is 4-7-membered heterocyclyl having 1-2 heteroatoms independently selected from the group consisting of nitrogen, oxygen, and sulfur.

In some embodiments, $R^x$ is hydrogen. In some embodiments, $R^x$ is an oxygen protecting group. In some embodiments, $R^x$ is an alkyl ethers. In some embodiments, $R^x$ is a benzyl ether. In some embodiments, $R^x$ is silyl ether. In some embodiments, $R^x$ is an acetal.

In some embodiments, $R^x$ is ketal. In some embodiments, $R^x$ is ester. In some embodiments, $R^x$ is carbamate. In some embodiments, $R^x$ is carbonate.

In some embodiments, $R^y$ is —OH. In some embodiments, $R^y$ is —OR. In some embodiments, $R^y$ is a carboxyl protecting group. In some embodiments, $R^y$ is an ester. In some embodiments, $R^y$ is an amide. In some embodiments, $R^y$ is a hydrazide.

In Annie embodiments, $R^s$ is

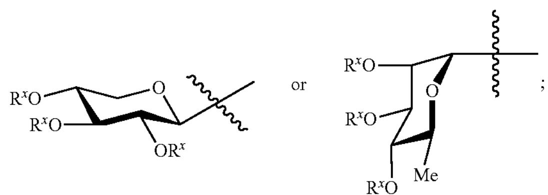

In some embodiments, $R^{x'}$ is optionally substituted 6-10-membered aryl. In some embodiments, $R^{x'}$ is optionally substituted $C_{1-6}$ aliphatic. In some embodiments, $R^{x'}$ is optionally substituted or $C_{1-6}$ heteroaliphatic having 1-2 heteroatoms independently selected from the group consisting of nitrogen, oxygen, and sulfur. In some embodiments, two $R^{x'}$ are taken together to form a 5-7-membered heterocyclic ring having 1-2 heteroatoms independently selected from the group consisting of nitrogen, oxygen, and sulfur.

In some embodiments, R is hydrogen. In some embodiments, R is an acyl. In some embodiments, R is arylalkyl. In some embodiments, R is 6-10-membered aryl. In some embodiments, R is $C_{1-6}$ aliphatic. In some embodiments, R is $C_{1-6}$ heteroaliphatic having 1-2 heteroatoms independently selected from the group consisting of nitrogen, oxygen, and sulfur. In some embodiments, two R on the same nitrogen atom are taken with the nitrogen atom to form a 4-7-membered heterocyclic ring having 1-2 heteroatoms independently selected from the group consisting of nitrogen, oxygen, and sulfur.

In some embodiments, $R^{1'}$ has the same embodiments as $R^1$.

Exemplary compounds of Formula I are set forth in Table 1 below:

TABLE 1

| EXEMPLARY COMPOUNDS OF FORMULA I |
| --- |
| 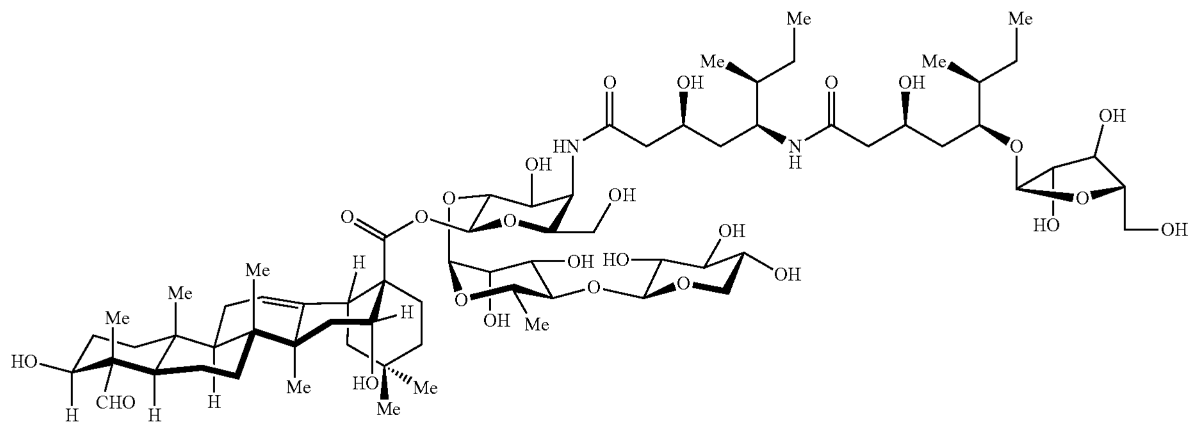<br>I-1 |
| 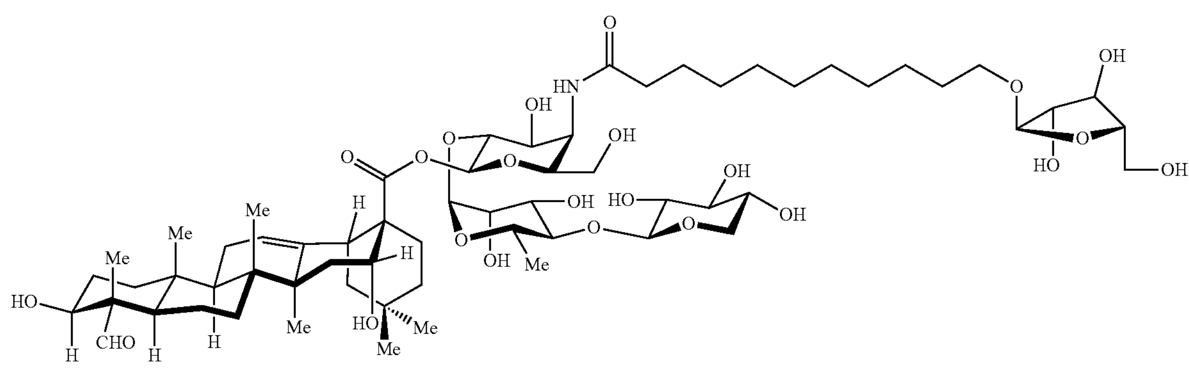<br>I-2 |
| 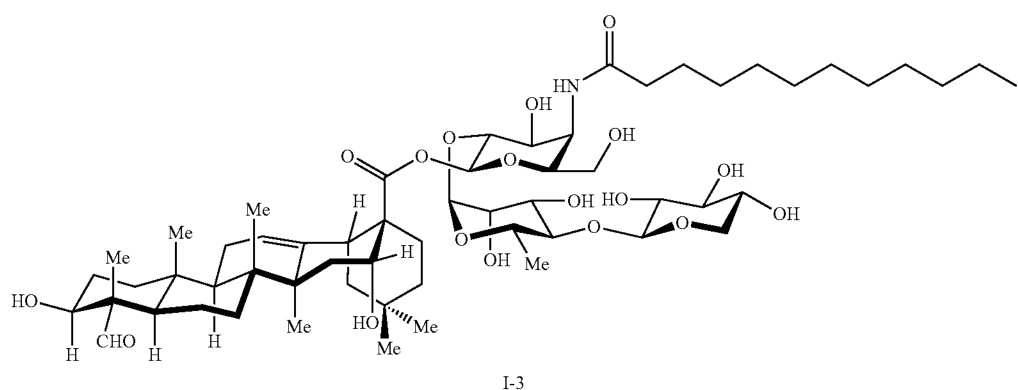<br>I-3 |

TABLE 1-continued
| EXEMPLARY COMPOUNDS OF FORMULA I |
| --- |
| 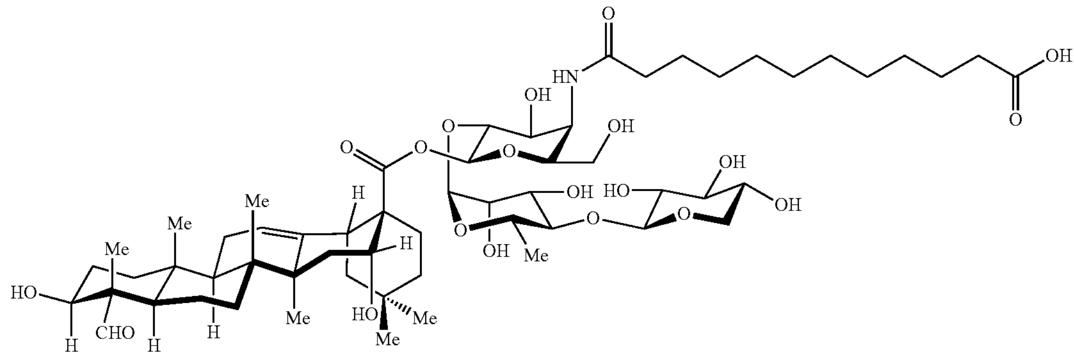<br><br>I-4 |
| 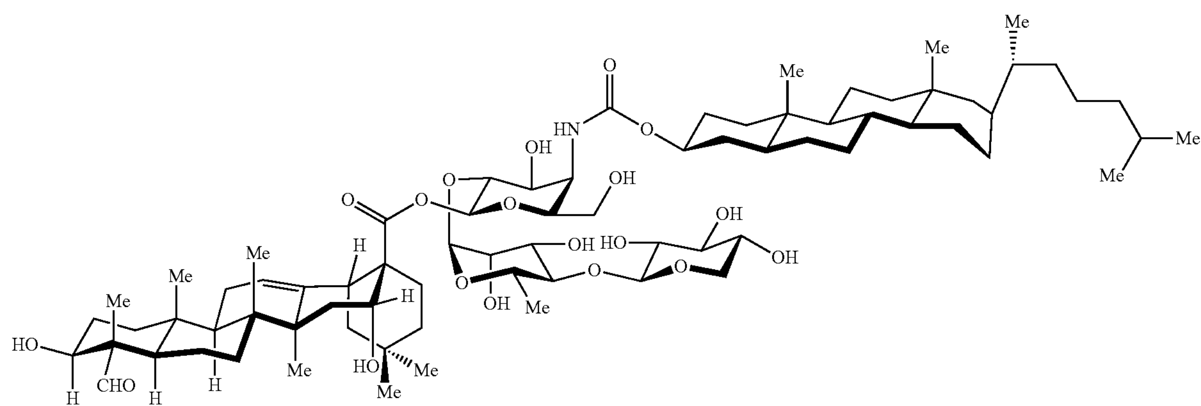<br><br>I-5 |
| 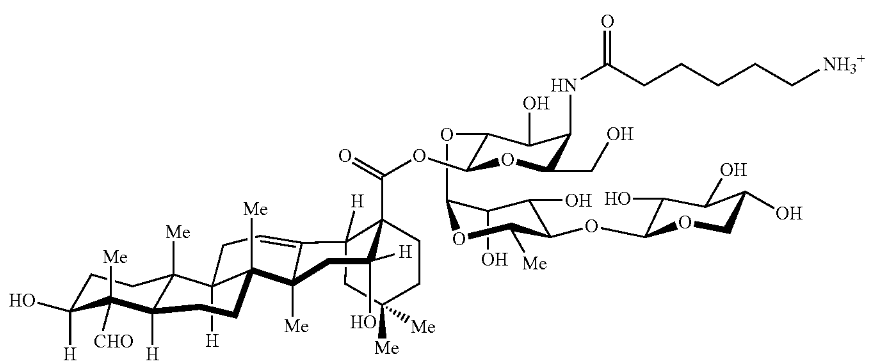<br><br>I-6 |

TABLE 1-continued

EXEMPLARY COMPOUNDS OF FORMULA I

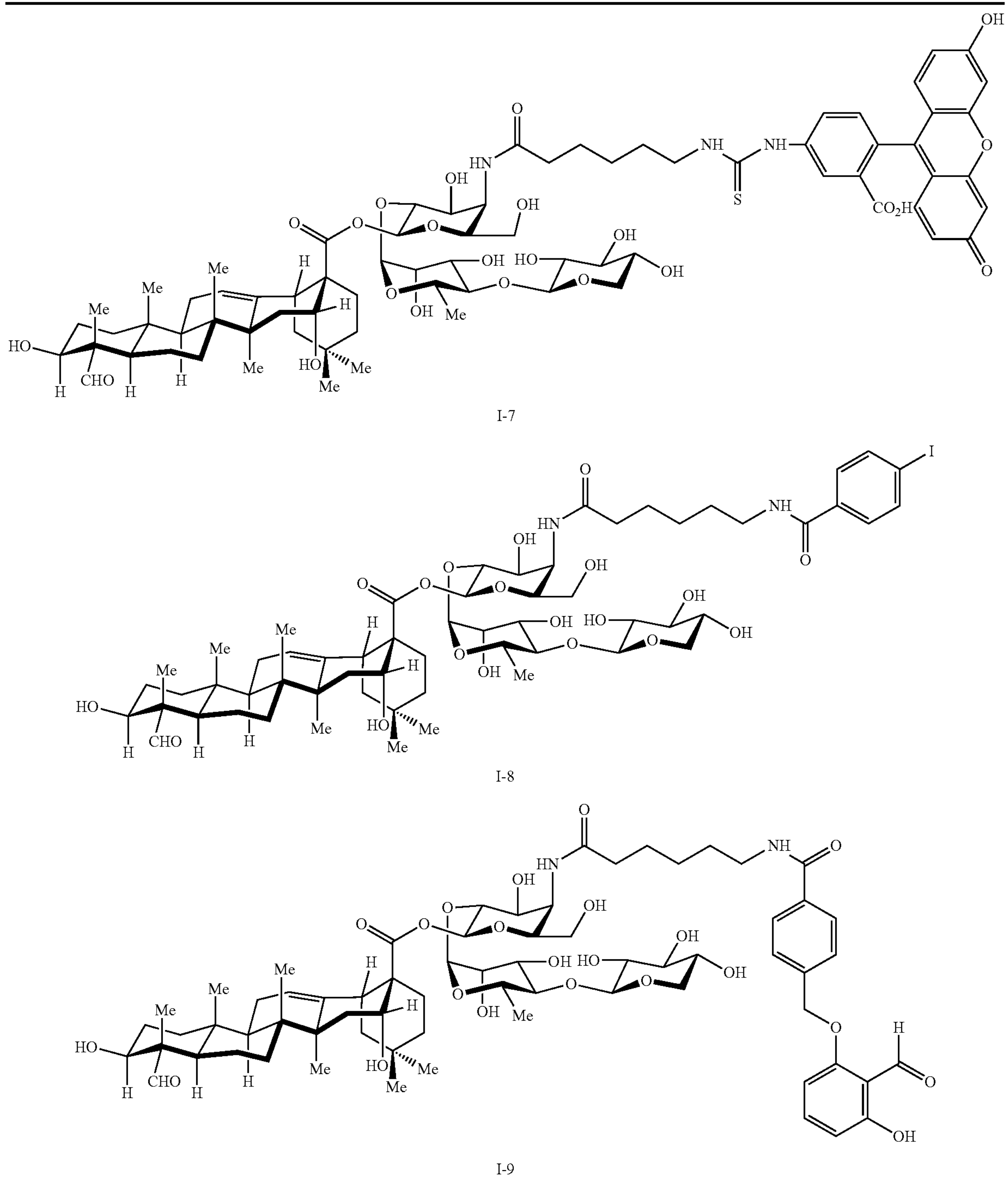

It will be appreciated that it is not an object of the present subject matter to claim compounds disclosed in the prior art that are the result of isolation or degradation studies on naturally occurring prosapogenins or saponins.

Synthesis of Compounds

As described in U.S. Ser. No. 12/420,803, issued as U.S. Pat. No. 8,283,456 (and its parent/child U.S. applications and publications), the synthesis of QS-21 and at least some of its analogues can be carried out in part by obtaining semi-purified abstract from *Quillaja saponaria* (commercially available as Quil-A, Accurate Chemical and Scientific Corporation, Westbury, N.Y.) comprising a mixture of at least 50 distinct saponin species (van Setten, D. C.; Vandewerken, G.; Zomer, G.; Kersten, G. F. A. *Rapid Commun. Mass Spectrom.* 1995, 9, 660-666). Many of said saponin species include a triterpene-trisaccharide substructure as found in immunologically-active *Quillaja saponins* such as QS-21 and QS-7. Exposing these saponin species to base hydrolysis affords a mixture enriched with prosapogenins A, B, and C (shown below).

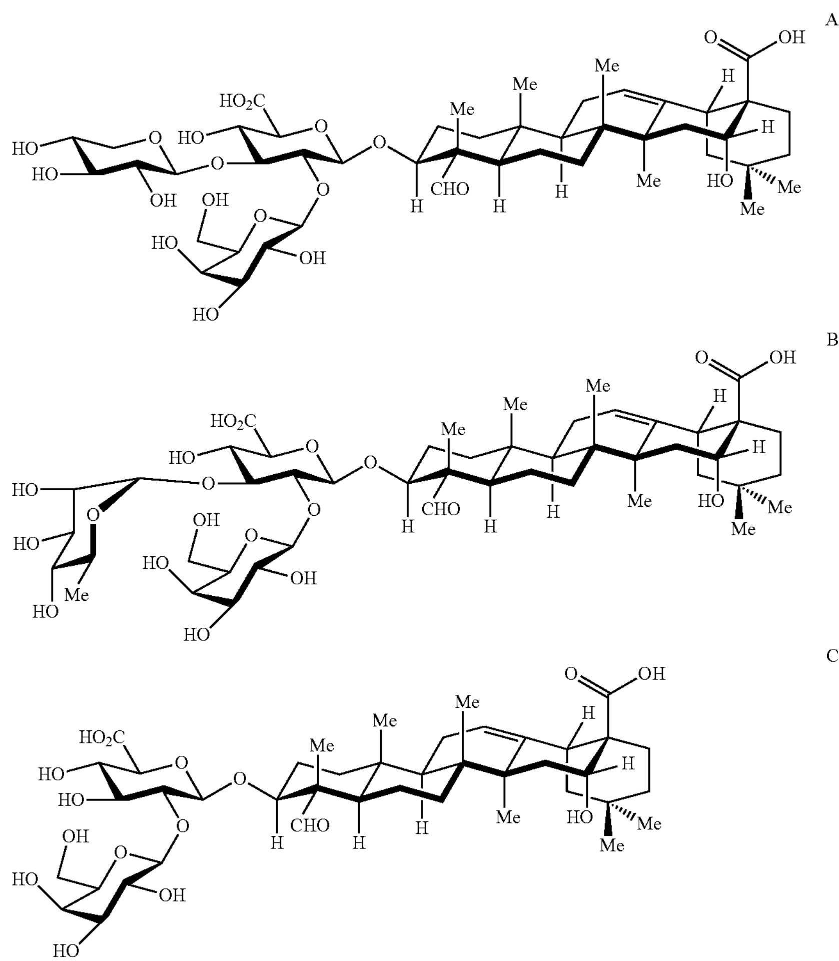

U.S. Ser. No. 12/420,803, issued as U.S. Pat. No. 8,283,456 (and its parent/child U.S. applications and publications) presents a strategy that allows for the facile separation of derivatized prosapogenins A, B, and C via silica gel chromatography. It will be appreciated that some embodiments of the present application may be synthesized in part using the methods described in U.S. Ser. No. 12/420,803, issued as U.S. Pat. No. 8,283,456 (and its parent/child U.S. applications and publications), particularly the methods relating to facile separation of derivatized prosapogenins A, B, and C. In one aspect, separated derivatized prosapogenins A, B, and/or C may then be used to synthesize QS-21 or analogs thereof using the methods described herein.

Adjuvants

Most protein and glycoprotein antigens are poorly immunogenic or non-immunogenic when administered alone. Strong adaptive immune responses to such antigens often requires the use of adjuvants. Immune adjuvants are substances that, when administered to a subject, increase the immune response to an antigen or enhance certain activities of cells from the immune system. An adjuvant may also allow the use of a lower dose of antigen to achieve a useful immune response in a subject.

Common adjuvants include alum, Freund's adjuvant (an oil-in-water emulsion with dead mycobacteria), Freund's adjuvant with MDP (an oil-in-water emulsion with muramyl dipeptide, MDP, a constituent of mycobacteria), alum plus *Bordetella pertussis* (aluminum hydroxide gel with killed *B. pertussis*). Such adjuvants are thought to act by delaying the release of antigens and enhancing uptake by macrophages. Immune stimulatory complexes (ISCOMs) are open cage-like complexes typically with a diameter of about 40 nm that are built up by cholesterol, lipid, immunogen, and saponin such as Quil-A (a *Quillaja saponin* extract). ISCOMs deliver antigen to the cytosol, and have been demonstrated to promote antibody response and induction of T helper cell as well as cytotoxic T lymphocyte responses in a variety of experimental animal models.

Natural saponin adjuvant QS-21 is far more potent than currently used adjuvants, like alum. QS-21's superiority over more than 20 other adjuvants tested in preclinical models and over 7 other adjuvants used in the clinic has been demonstrated. Thus, QS-21 has been widely used despite its three major liabilities: dose limiting toxicity, poor stability, and the limited availability of quality product.

Use of QS-21 as an adjuvant has been associated with notable adverse biological effects. In humans, QS-21 has displayed both local and systemic toxicity. Maximum doses for cancer patients are 100-150 μg and for healthy patients are typically 50 μg (an immunology suboptimal dose). As a result, clinical success of non-cancer vaccines depends upon the identification of novel, potent adjuvants that are more tolerable.

The present application encompasses the recognition that synthetic access to and structural modification of QS-21 and related *Quillaja saponins* may afford compounds with high adjuvant potency and low toxicity, as well as having more stability and being more cost effective.

Vaccines

Compositions in this application are useful as vaccines to induce active immunity towards antigens in subjects. Any animal that may experience the beneficial effects of the compositions of the present application is within the scope of subjects that may be treated. In some embodiments, the subjects are mammals. In some embodiments, the subjects are humans.

The vaccines of the present application may be used to confer resistance to infection by either passive or active immunization. When the vaccines of the present application are used to confer resistance through active immunization, a vaccine of the present application is administered to an animal to elicit a protective immune response which either prevents or attenuates a proliferative or infectious disease. When the vaccines of the present application are used to confer resistance to infection through passive immunization, the vaccine is provided to a host animal (e.g., human, dog, or mouse), and the antisera elicited by this vaccine is recovered and directly provided to a recipient suspected of having an infection or disease or exposed to a causative organism.

The present application thus concerns and provides a means for preventing or attenuating a proliferative disease resulting from organisms which have antigens that are recognized and bound by antisera produced in response to the immunogenic antigens included in vaccines of the present application. As used herein, a vaccine is said to prevent or attenuate a disease if its administration to an animal results either in the total or partial attenuation (i.e., suppression) of a symptom or condition of the disease, or in the total or partial immunity of the animal to the disease.

The administration of the vaccine (or the antisera which it elicits) may be for either a "prophylactic" or "therapeutic" purpose. When provided prophylactically, the vaccine(s) are provided in advance of any symptoms of proliferative disease. The prophylactic administration of the vaccine(s) serves to prevent or attenuate any subsequent presentation of the disease. When provided therapeutically, the vaccine(s) is provided upon or after the detection of symptoms which indicate that an animal may be infected with a pathogen. The therapeutic administration of the vaccine(s) serves to attenuate any actual disease presentation. Thus, the vaccines may be provided either prior to the onset of disease proliferation (so as to prevent or attenuate an anticipated infection) or after the initiation of an actual proliferation.

Thus, in one aspect the present application provides vaccines comprising a T cell antigen. In another aspect, such T cell antigens are patient- and/or tumor-specific peptide antigens. In some embodiments, such T cell antigens may be derived or identified using neo-antigen screening or similar methods. In other embodiments, such T cell antigens may be derived or identified using other methods of selection. In further embodiments, such T cell antigens arise as a consequence of tumor-specific mutations. In yet another aspect, such T cell antigens are a class of HLA-bound peptides.

One aspect of the present application relates to adjuvant and antigen vaccine compositions that give rise to vaccine-induced polyfunctional $CD4^+$ and/or $CD8^+$ T cells targeted to tumor-specific neo-antigens. In particular, the adjuvant compositions according to the present application provide superior responses in such vaccines as compared to other types of adjuvants. In another aspect, the present application relates to methods of administering adjuvant and antigen vaccine compositions that give rise to vaccine-induced polyfunctional $CD4^+$ and/or $CD8^+$ T cells targeted to tumor-specific neo-antigens. In yet another embodiment, the present application relates to methods of preparing adjuvant and antigen vaccine compositions that give rise to vaccine-induced polyfunctional $CD4^+$ and/or $CD8^+$ T cells targeted to tumor-specific neo-antigens.

One of ordinary skill in the art will appreciate that vaccines may optionally include a pharmaceutically acceptable excipient or carrier. Thus, according to another aspect, provided vaccines may comprise one or more antigens that are optionally conjugated to a pharmaceutically acceptable excipient or carrier. In some embodiments, said one or more antigens are conjugated covalently to a pharmaceutically acceptable excipient. In other embodiments, said one or more antigens are non-covalently associated with a pharmaceutically acceptable excipient.

As described above, adjuvants may be used to increase the immune response to an antigen. According to the present application, provided vaccines may be used to invoke an immune response when administered to a subject. In certain embodiments, an immune response to an antigen may be potentiated by administering to a subject a provided vaccine in an effective amount to potentiate the immune response of said subject to said antigen.

Formulations

The compounds of the present application may be combined with a pharmaceutically acceptable excipient to form a pharmaceutical composition. In certain embodiments, formulations of the present application include injectable formulations. In certain embodiments, the pharmaceutical composition includes a pharmaceutically acceptable amount of a compound of the present application. In certain embodiments, the compounds of the application and an antigen form an active ingredient. In certain embodiments, the compound of the present application alone forms an active ingredient. The amount of active ingredient(s) which can be combined with a carrier material to produce a single dosage form will vary depending upon the host being treated, and the particular mode of administration. The amount of active ingredient(s) that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%, or from about 1% to 99%, preferably from 10% to 90%, 20% to 80%, 30% to 70%, 40% to 60%, 45% to 55%, or about 50%.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Non-limiting examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Non-limiting examples of suitable aqueous and nonaqueous carriers, which may be employed in the pharmaceutical compositions of the present application include water, alcohols (including but not limited to methanol, ethanol, butanol, etc.), polyols (including but not limited to glycerol, propylene glycol, polyethylene glycol, etc.), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain additives such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a formulation, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form.

Regardless of the route of administration selected, the compounds of the present application, which may be used in a suitable hydrated form, and/or the pharmaceutical compositions of the present application, are formulated into pharmaceutically-acceptable dosage forms by conventional methods known to those of skill in the art.

Actual dosage levels of the active ingredients in the pharmaceutical compositions of the present application may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present application employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the present application employed in the pharmaceutical composition at levels lower than that required to achieve the desired therapeutic effect and then gradually increasing the dosage until the desired effect is achieved.

In some embodiments, a compound or pharmaceutical composition of the present application is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the present application repeatedly over the life of the subject. Preferred chronic treatments involve regular administrations, for example one or more times a day, one or more times a week, or one or more times a month. In general, a suitable dose, such as a daily dose of a compound of the present application, will be that amount of the compound that is the lowest dose effective to produce a therapeutic effect. Such an effective dose will generally depend upon the factors described above.

Generally, doses of the compounds of the present application for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight. However, lower or higher doses can be used. In some embodiments, the dose administered to a subject may be modified as the physiology of the subject changes due to age, disease progression, weight, or other factors.

In some embodiments, provided adjuvant compounds of the present application are administered as pharmaceutical compositions or vaccines. In certain embodiments, it is contemplated that the amount of adjuvant compound administered will be 1-2000 μg. In certain embodiments, it is contemplated that the amount of adjuvant compound administered will be 1-1000 μg. In certain embodiments, it is contemplated that the amount of adjuvant compound administered will be 1-500 μg. In certain embodiments, it is contemplated that the amount of adjuvant compound administered will be 1-250 μg. In certain embodiments, it is contemplated that the amount of adjuvant compound administered will be 100-1000 μg. In certain embodiments, it is contemplated that the amount of adjuvant compound administered will be 100-500 μg. In certain embodiments, it is contemplated that the amount of adjuvant compound administered will be 100-200 μg. In certain embodiments, it is contemplated that the amount of adjuvant compound administered will be 250-500 μg. In certain embodiments, it is contemplated that the amount of adjuvant compound administered will be 10-1000 μg. In certain embodiments, it is contemplated that the amount of adjuvant compound administered will be 500-1000 μg. In certain embodiments, it is contemplated that the amount of adjuvant compound administered will be 50-250 μg. In certain embodiments, it is contemplated that the amount of adjuvant compound administered will be 50-500 μg.

In some embodiments, provided adjuvant compounds of the present application are administered as pharmaceutical compositions or vaccines. In certain embodiments, it is contemplated that the amount of adjuvant compound administered will be 1-2000 mg. In certain embodiments, it is contemplated that the amount of adjuvant compound administered will be 1-1000 mg. In certain embodiments, it is contemplated that the amount of adjuvant compound administered will be 1-500 mg. In certain embodiments, it is contemplated that the amount of adjuvant compound administered will be 1-250 mg. In certain embodiments, it is contemplated that the amount of adjuvant compound administered will be 100-1000 mg. In certain embodiments, it is contemplated that the amount of adjuvant compound administered will be 100-500 mg. In certain embodiments, it is contemplated that the amount of adjuvant compound administered will be 100-200 mg. In certain embodiments, it is contemplated that the amount of adjuvant compound administered will be 250-500 mg. In certain embodiments, it is contemplated that the amount of adjuvant compound administered will be 10-1000 mg. In certain embodiments, it is contemplated that the amount of adjuvant compound administered will be 500-1000 mg. In certain embodiments, it is contemplated that the amount of adjuvant compound administered will be 50-250 mg. In certain embodiments, it is contemplated that the amount of adjuvant compound administered will be 50-500 mg. In certain embodiments, it is contemplated that the amount of adjuvant compound administered will be 0.01-215.4 mg.

In certain embodiments, it is contemplated that the amount of adjuvant administered will be 1000-5000 μg/kg. In certain embodiments, it is contemplated that the amount of adjuvant administered will be 1000-4000 μg/kg. In certain embodiments, it is contemplated that the amount of adjuvant administered will be 1000-3000 μg/kg. In certain embodiments, it is contemplated that the amount of adjuvant administered will be 1000-2000 μg/kg. In certain embodiments, it is contemplated that the amount of adjuvant administered will be 2000-5000 μg/kg. In certain embodiments, it is contemplated that the amount of adjuvant administered will be 2000-4000 μg/kg. In certain embodiments, it is contemplated that the amount of adjuvant administered will be 2000-3000 μg/kg. In certain embodiments, it is contemplated that the amount of adjuvant administered will be 3000-5000 μg/kg. In certain embodiments, it is contemplated that the amount of adjuvant administered will be 3000-4000 μg/kg. In certain embodiments, it is contemplated that the amount of adjuvant administered will be 4000-5000 μg/kg. In certain embodiments, it is contemplated that the amount of adjuvant administered will be 1-500 μg/kg. In certain embodiments, it is contemplated that the amount of adjuvant administered will be 500-1000 μg/kg. In certain embodiments, it is contemplated that the amount of adjuvant administered will be 1000-1500 μg/kg. In certain embodiments, it is contemplated that the amount of adjuvant administered will be 1 mg/kg. In certain embodiments, it is contemplated that the amount of adjuvant administered will be 2 mg/kg. In certain embodiments, it is contemplated that the amount of adjuvant administered will be 3 mg/kg. In certain embodiments, it is contemplated that the amount of adjuvant administered will be 4 mg/kg. In certain embodiments, it is contemplated that the amount of adjuvant administered will be 5 mg/kg. In certain embodiments, it is contemplated that the amount of adjuvant administered will be 0.0029-5 mg/kg. In certain embodiments, the amount of adjuvant administered in females is less than the amount of adjuvant administered in males. In certain embodiments, the amount of adjuvant administered to infants is less than the amount of adjuvant administered to adults. In certain embodiments, the amount of adjuvant administered to pediatric recipients is less than the amount of adjuvant administered to adults. In certain embodiments, the amount of adjuvant administered to immunocompromised recipients is more than the amount of adjuvant administered to healthy recipients. In certain embodiments, the amount of adjuvant administered to elderly recipients is more than the amount of adjuvant administered to non-elderly recipients.

If desired, the effective dose of the active compound may be administered as two, three, four, five, six or more sub-doses administered separately at appropriate intervals throughout the day, optionally, in unit dosage forms.

While it is possible for a compound of the present application to be administered alone, in certain embodiments the compound is administered as a pharmaceutical formulation or composition as described above.

The compounds according to the present application may be formulated for administration in any convenient way for use in human or veterinary medicine, by analogy with other pharmaceuticals.

The present application provides kits comprising pharmaceutical formulations or compositions of a compound of the present application. In certain embodiments, such kits include the combination of a compound of formulae I and/or II and an antigen. The agents may be packaged separately or together. The kit optionally includes instructions for prescribing the medication. In certain embodiments, the kit includes multiple doses of each agent. The kit may include sufficient quantities of each component to treat one or more subject for a week, two weeks, three weeks, four weeks, or multiple months. The kit may include a full cycle of immunotherapy. In some embodiments, the kit includes a vaccine comprising one or more bacterial or viral-associated antigens, and one or more provided compounds.

EXAMPLES

Example 1: Total Synthesis of Compound I-4 (TQL-1055)

Figure 9:
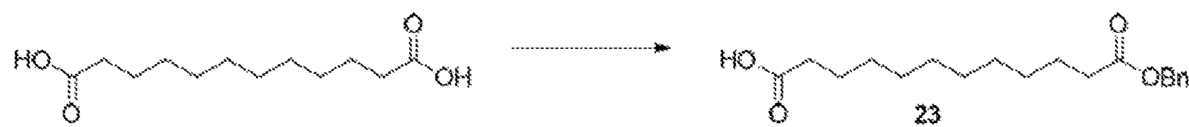
FIG. 9 depicts one synthetic route to obtain an intermediate used in the total synthesis of Compound I-4 (TiterQuil-1-0-5-5/TQL-1055).
Figure 10:
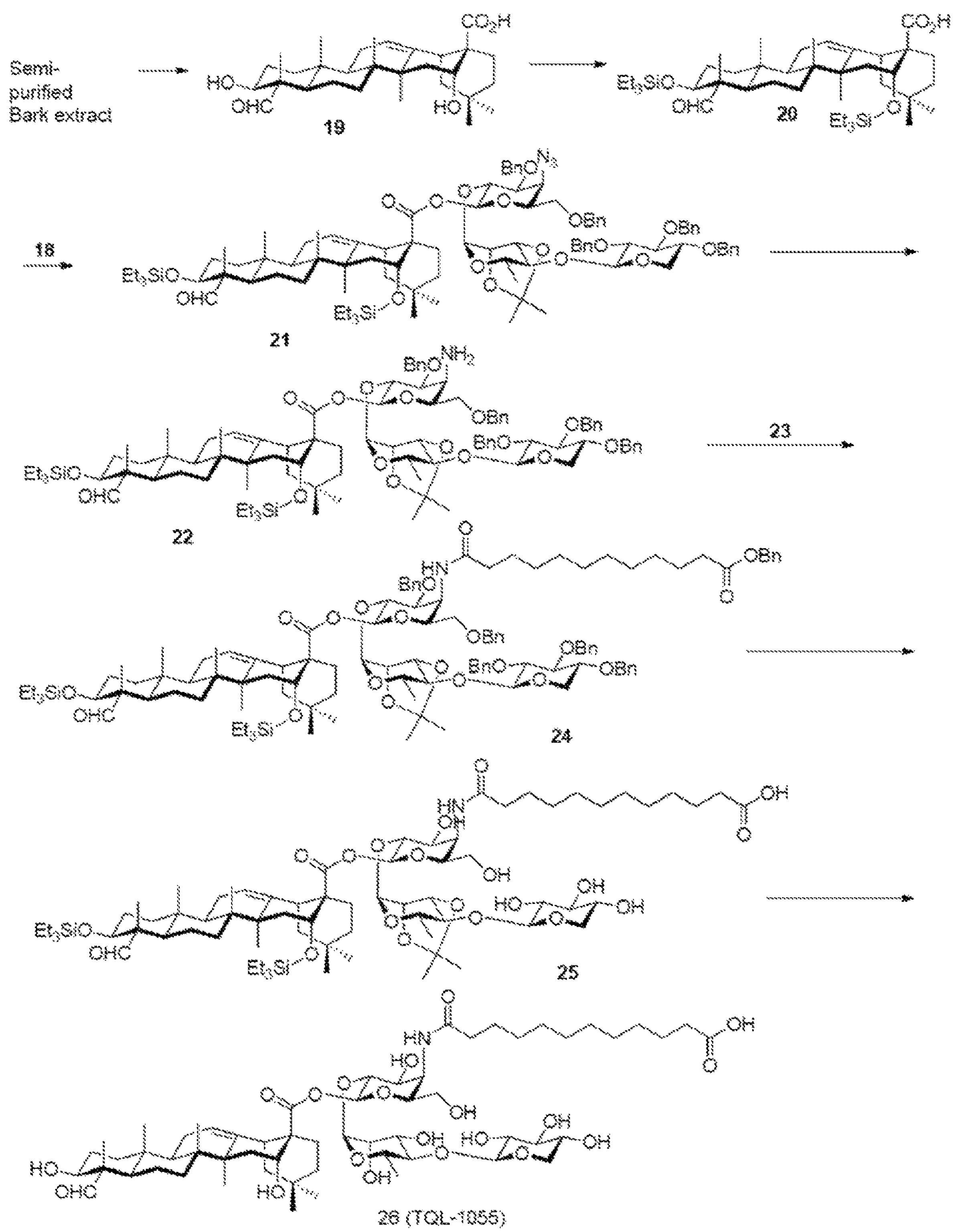
FIG. 10 depicts the total synthesis to obtain Compound I-4 (TiterQuil-1-0-5-5/TQL-1055). In this figure, "Semi-purified Bark extract" is the semi-purified abstract from *Quillaja saponaria.*

The total synthesis of Compound I-4 (TiterQuil-1-0-5-5/TQL-1055) is depicted in FIG. 9-11 of the present application. The numbering associated with the compounds in this example is not meant to correspond with other formula or compound numbering appearing throughout the remainder of the application, including other Figures, the claims, or Examples 1-9.

Example 2: Evaluation of Compound I-4 (TiterQuil-1-0-5-5/TQL-1055) Adjuvant for Peptide Vaccines The impact of synthetic TQL-1055 (Compound I-4) on CD4 and CD8 T cell responses to peptides was tested in mice as a single adjuvant and in combination with Genocea Biosciences GEN-AS2 adjuvant and sGenocea Biosciences GEN-AS3 adjuvant according to the plan in the table below. The GEN-AS2 and GEN-AS3 adjuvant are TLR agonist-based adjuvant systems. Specific peptides tested include Genocea synthetic long peptides (SLPs) GB208_1, GB208_4, GB208_8, which are tumor-specific T cell antigens identified by neo-antigen screening, however the results are expected to replicate to other types of peptides. Combinations including an adjuvant composition with the SLPs were administered to mice via s.c. scruff according to the plan below. Injections were administered to groups according to the plan in the table below. Responses in mice were measured seven (7) or fourteen (14) days after the final injection.

TABLE 2

| EXPERIMENTAL DESIGN OF EXAMPLE 2 | | | | |
|---|---|---|---|---|
| Group # | # Mice | Antigen | Adjuvant | Schedule (injection days) |
| 1 | 4 | PBS (phosphate buffered isotonic saline | None | 0, 7 |
| 2 | 4 | None | 50 μg TQL-1055 | 0, 7 |
| 3 | 5 | 150 μg SLPs GB208_1, _4, _8 | GEN-AS3 | 0, 7 |
| 4 | 5 | 150 μg SLPs GB208_1, _4, _8 | GEN-AS2 | 0, 7 |
| 5 | 5 | 150 μg SLPs GB208_1, _4, _8 | 10 μg TQL-1055 | 0, 7 |
| ©¢6 | 5 | 150 μg SLPs GB208_1, _4, _8 | 25 μg TQL-1055 | 0, 7 |
| 7 | 5 | 150 μg SLPs GB208_1, _4, _8 | 50 μg TQL-1055 | 0, 7 |
| 8 | 5 | 150 μg SLPs GB208_1, _4, _8 | 100 μg TQL-1055 | 0, 7 |
| 9 | 5 | 150 μg SLPs GB208_1, _4, _8 | 50 μg TQL-1055 + GEN-AS2 | 0, 7 |
| 10 | 5 | 150 μg SLPs GB208_1, _4, _8 | 10 μg TQL-1055 + GEN-AS2 | 0, 7 |
| 11 | 5 | 150 μg SLPs GB208_1, _4, _8 | 50 μg TQL-1055 | 0, 14 |
| 12 | 5 | 150 μg SLPs GB208_1, _4, _8 | 50 μg TQL-1055 + GEN-AS2 | 0, 14 |

T cell responses were measured by the following ELISPOT analyses:

1. Total splenocytes:
   a. Combined responses to GB208_1, _4, _8; re-stimulation with overlapping peptides (OLPs) at 10 μg/ml;
   b. Responses to GB208_1; re-stimulation GB208_1 at 10 μg/ml;
   c. Responses to GB208_4; re-stimulation GB208_4 at 10 μg/ml;
   d. Responses to GB208_8; re-stimulation GB208_8 at 10 μg/ml;
2. CD4 enriched: combined responses to GB208_1, _4, _8; re-stimulation with overlapping peptides at 20 μg/ml; and
3. CD8 enriched: combined responses to GB208_1, _4, _8; re-stimulation with overlapping peptides at 20 μg/ml.

Specific resulting data is shown in FIGS. 2-8 and in the tables below.

Tables 3a-h. Results from Experiment in Example 2

The values in Tables 3a-f results are spot forming units per 800,000 cells. A value of 2000 was used if spots exceeded the upper limit of detection. All groups had n=5, except groups 1, 2, and 3, which had four mice in each group.

TABLE 3a

| Media Alone | | | | | |
|---|---|---|---|---|---|
| Group # | Mouse 1 | Mouse 2 | Mouse 3 | Mouse 4 | Mouse 5 |
| 1 | 0 | 0 | 0 | 0 | |
| 2 | 0 | 0 | 0.5 | 0 | |
| 3 | 0 | 2 | 0 | 2.5 | 0 |
| 4 | 0 | 2.5 | 4.5 | 0.5 | 0.5 |
| 5 | 0 | 0 | 0 | 4 | 2 |
| 6 | 0 | 0 | 0 | 0.5 | 0.5 |
| 7 | 0 | 0.5 | 0 | 0 | 0 |
| 8 | 1.5 | 0 | 0 | 0 | 1.5 |
| 9 | 0 | 0.5 | 0 | 0.5 | 0.5 |
| 10 | 0 | 0 | 0.5 | 0 | 0.5 |
| 11 | 0 | 0 | 0 | 0 | 0 |
| 12 | 14 | 0 | 1 | 3 | 7.5 |

TABLE 3b

| SLP1-specific INFγ responses in splenocytes | | | | | |
|---|---|---|---|---|---|
| Group # | Mouse 1 | Mouse 2 | Mouse 3 | Mouse 4 | Mouse 5 |
| 1 | 0 | 0 | 1 | 0 | |
| 2 | 0 | 0 | 0 | 0 | |
| 3 | 493 | 1099 | 78 | 136 | 127 |
| 4 | 6 | 5 | 7 | 0 | 8 |
| 5 | 0 | 4 | 0 | 11 | 5 |
| 6 | 3 | 4 | 25 | 12 | 30 |
| 7 | 3 | 13 | 4 | 18 | 25 |
| 8 | 0 | 5 | 7 | 29 | 3 |
| 9 | 959 | 2000 | 2000 | 2000 | 1042 |
| 10 | 131 | 378 | 278 | 600 | 548 |
| 11 | 3 | 20 | 3 | 94 | 4 |
| 12 | 879 | 2000 | 2000 | 2000 | 625 |

TABLE 3c

| SLP4-specific INFγ responses in splenocytes | | | | | |
|---|---|---|---|---|---|
| Group # | Mouse 1 | Mouse 2 | Mouse 3 | Mouse 4 | Mouse 5 |
| 1 | 0 | 0 | 0 | 0 | |
| 2 | 0 | 0 | 0 | 0 | |
| 3 | 1191 | 2000 | 948 | 2000 | 2000 |
| 4 | 280 | 147 | 139 | 155 | 60 |
| 5 | 31 | 135 | 21 | 183 | 72 |
| 6 | 102 | 70 | 431 | 22 | 169 |
| 7 | 68 | 23 | 142 | 93 | 42 |
| 8 | 30 | 37 | 19 | 76 | 78 |
| 9 | 2000 | 2000 | 2000 | 2000 | 2000 |
| 10 | 1151 | 598 | 2000 | 506 | 739 |
| 11 | 43 | 96 | 31 | 258 | 79 |
| 12 | 2000 | 2000 | 2000 | 2000 | 2000 |

TABLE 3d

| SLP8-specific INFγ responses in splenocytes | | | | | |
|---|---|---|---|---|---|
| Group # | Mouse 1 | Mouse 2 | Mouse 3 | Mouse 4 | Mouse 5 |
| 1 | 0 | 1 | 0 | 0 | |
| 2 | 0 | 0 | 2 | 0 | |
| 3 | 294 | 324 | 704 | 298 | 406 |
| 4 | 14 | 12 | 16 | 1 | 20 |
| 5 | 0 | 13 | 0 | 15 | 16 |
| 6 | 21 | 5 | 53 | 3 | 21 |
| 7 | 29 | 5 | 55 | 286 | 20 |

TABLE 3d-continued

| SLP8-specific INFγ responses in splenocytes | | | | | |
|---|---|---|---|---|---|
| Group # | Mouse 1 | Mouse 2 | Mouse 3 | Mouse 4 | Mouse 5 |
| 8 | 15 | 0 | 2 | 29 | 4 |
| 9 | 706 | 2000 | 1182 | 757 | 2000 |
| 10 | 173 | 459 | 251 | 1013 | 285 |
| 11 | 59 | 33 | 93 | 164 | 136 |
| 12 | 2000 | 2000 | 2000 | 2000 | 2000 |

TABLE 3e

| INFγ responses in splenocytes to SLPs 1, 4, 8 | | | | | |
|---|---|---|---|---|---|
| Group # | Mouse 1 | Mouse 2 | Mouse 3 | Mouse 4 | Mouse 5 |
| 1 | 0.5 | 1 | 0.5 | 2 | |
| 2 | 0.5 | 2.5 | 0.5 | 2 | |
| 3 | 2000 | 2000 | 2000 | 2000 | 2000 |
| 4 | 256.5 | 116 | 129 | 112.5 | 61 |
| 5 | 12.5 | 20 | 11 | 115 | 53 |
| 6 | 104.5 | 39 | 338 | 12.5 | 167.5 |
| 7 | 56 | 32 | 138 | 139 | 59.5 |
| 8 | 42.5 | 22 | 17 | 74.5 | 73 |
| 9 | 2000 | 2000 | 2000 | 2000 | 2000 |
| 10 | 1046.5 | 762.5 | 1346.5 | 992 | 957 |
| 11 | 70 | 85 | 32.5 | 319.5 | 112 |
| 12 | 2000 | 2000 | 2000 | 2000 | 2000 |

TABLE 3f

| INFγ responses in splenocytes to PMA lonomycin control | | | | | |
|---|---|---|---|---|---|
| Group # | Mouse 1 | Mouse 2 | Mouse 3 | Mouse 4 | Mouse 5 |
| 1 | 221.5 | 189.5 | 263.5 | 212 | |
| 2 | 168.5 | 181 | 168 | 256 | |
| 3 | 94.5 | 186 | 177 | 242 | 298.5 |
| 4 | 418.5 | 260 | 336.5 | 358.5 | 433 |
| 5 | 390 | 342.5 | 386.5 | 467 | 675.5 |
| 6 | 326 | 181.5 | 224.5 | 461 | 339 |
| 7 | 200 | 234 | 243.5 | 343 | 183 |
| 8 | 130.5 | 166.5 | 165 | 232 | 286.5 |
| 9 | 337 | 392 | 313 | 525.5 | 417.5 |
| 10 | 296 | 298.5 | 281 | 360 | 258.5 |
| 11 | 126.5 | 186 | 348 | 456 | 387 |
| 12 | 546.5 | 524.5 | 473.5 | 574 | 549.5 |

The values in Tables 3g-h results are spot forming units per 500,000 cells. A value of 2000 was used if spots exceeded the upper limit of detection. Table 3g shows combined CD4 responses. Table 3f shows combined CD8 responses.

TABLE 3g

| CD4 Responses | | | |
|---|---|---|---|
| Group # | Media Alone | OLP pool SLP 1, 4, 8 | PMA/lonomycin control |
| 1 | 0 | 0 | 406 |
| 2 | 0.5 | 0 | 411 |
| 3 | 1 | 2000 | 592 |
| 4 | 0 | 145.5 | 482 |
| 5 | 0 | 48.5 | 627.5 |
| 6 | 0 | 149.5 | 622 |
| 7 | 0 | 88.5 | 521 |
| 8 | 0 | 28.5 | 616.5 |
| 9 | 0 | 2000 | 512 |
| 10 | 0 | 766.5 | 374 |
| 11 | 0 | 79 | 292 |
| 12 | 0.5 | 2000 | 343 |

TABLE 3f

| CD8 Responses | | | |
|---|---|---|---|
| Group # | Media Alone | OLP pool SLP 1, 4, 8 | PMA/lonomycin control |
| 1 | 0 | 5 | 377 |
| 2 | 0.5 | 2.5 | 381.5 |
| 3 | 0.5 | 15.5 | 451 |
| 4 | 0 | 1 | 354 |
| 5 | 0 | 6.5 | 411 |
| 6 | 0.5 | 5 | 329.5 |
| 7 | 0 | 5.5 | 409 |
| 8 | 0 | 6.5 | 274 |
| 9 | 0 | 183 | 136.5 |
| 10 | 0 | 9 | 224 |
| 11 | 0 | 3.5 | 116 |
| 12 | 1 | 24 | 235 |

TABLE 4

| TQL-1055 COMBINATION RESPONSES VS. GEN-AS3 IN EXAMPLE 2 | | | | | | | |
|---|---|---|---|---|---|---|---|
| | Group 2 GEN-AS3 (D 0, 7) | Group 9 50 μg TQL-1055 + GEN-AS2 (D 0, 7) | | Group 10 10 μg TQL-1055 + GEN-AS2 (D 0, 7) | | Group 12 50 μg TQL-1055 + GEN-AS2 (D 0, 14) | |
| adjuvant | Mean SFU | Mean SFU | % GEN-AS3 | Mean SFU | % GEN-AS3 | Mean SFU | % GEN-AS3 |
| splenocyte OLP (1 μg/ml) | 2000 | 2000 | 100.0 | 1020.9 | 51.0 | 2000 | 100.0 |
| splenocyte GB208_1 (10 μg/ml) | 386.6 | 1600.2 | 413.9 | 387 | 100.1 | 1500.8 | 388.2 |
| splenocyte GB208_4 (10 μg/ml) | 1627.8 | 2000 | 122.9 | 998.8 | 61.4 | 2000 | 122.9 |
| splenocyte GB208_8 (10 μg/ml) | 405.2 | 1329 | 328.0 | 436.2 | 107.7 | 2000 | 100.0 |

TABLE 4-continued

TQL-1055 COMBINATION RESPONSES VS. GEN-AS3 IN EXAMPLE 2

| | Group 2 GEN-AS3 (D 0, 7) | Group 9 50 μg TQL-1055 + GEN-AS2 (D 0, 7) | | Group 10 10 μg TQL-1055 + GEN-AS2 (D 0, 7) | | Group 12 50 μg TQL-1055 + GEN-AS2 (D 0, 14) | |
|---|---|---|---|---|---|---|---|
| adjuvant | Mean SFU | Mean SFU | % GEN-AS3 | Mean SFU | % GEN-AS3 | Mean SFU | % GEN-AS3 |
| sorted CD4 OLP (20 μg/ml) | 2000 | 2000 | 100.0 | 766.5 | 38.3 | 2000 | 100.0 |
| sorted CD8 OLP (20 μg/ml) | 15.5 | 183 | 1180.6 | 9 | 58.1 | 24 | 154.8 |

Based on the results described above and shown in FIG. 2, TQL-1055 elicits potent T cell responses to peptides when used in combination with GEN-AS2 adjuvant. Specifically, a surprising and significant synergistic effect was observed between GEN-AS2 and TQL-1055, in which the combination elicits ≥8× better T-cell (CD4 and CD8) responses compared to GEN-AS2 alone or TQL-1055 alone. Such an effect between a TLR agonist-based adjuvant and TQL-1055 has not been observed to date and this significant synergistic interaction is surprising and would not have been expected by a person of ordinary skill in the art.

Based on the results described above and shown in FIG. 3, TQL-1055 combination with GEN-AS2 stimulates better peptide 1-specific T cell responses than GEN-AS3.

Based on the results described above and shown in FIG. 4, TQL-1055 combination with GEN-AS2 stimulates better peptide 4-specific T cell responses than GEN-AS3.

Based on the results described above and shown in FIG. 5, TQL-1055 combination with GEN-AS2 stimulates better peptide 8-specific T cell responses than GEN-AS3.

Based on the results described above and shown in FIG. 6, TQL-1055 combination with GEN-AS2 stimulates CD4 in line with GEN-AS3 and stimulates CD8 better than GEN-AS3.

Based on the results described above and shown in FIG. 7, TQL-1055, alone or in combination with GEN-AS2, can stimulate antibody response for antibodies specific to GB208_1, _4, and _8 either in line with or better than GEN-AS3.

Accordingly, the groups administered with TQL-1055 and the GEN-AS2 combination were consistently the best performers in all T cell analyses in this test. Responses to less immunogenic peptides (GB208_1, _8) was significantly better with TQL-1055+GEN-AS2 compared to GEN-AS3. The TQL-1055+GEN-AS2 combination also can enhance antibody response in line with or better than GEN-AS3.

The invention claimed is:

1. A pharmaceutical combination comprising:

a toll-like receptor (TLR) agonist-based adjuvant system, and

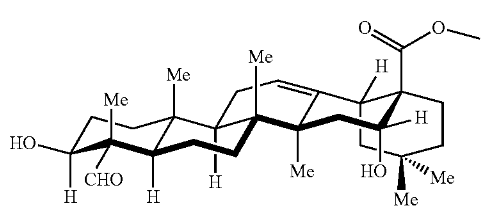

-continued

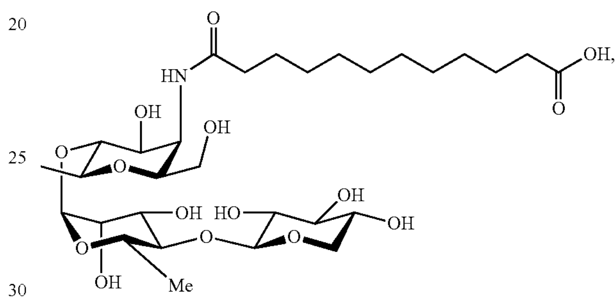

or a pharmaceutically acceptable salt thereof.

2. The pharmaceutical combination according to claim 1, further comprising an antigen.

3. The pharmaceutical combination according to claim 2, wherein the antigen is a peptide antigen.

4. The pharmaceutical combination according to claim 3, wherein the antigen is a tumor-specific antigen.

5. A method of stimulating the immune system of a mammal, comprising administering the pharmaceutical combination according to claim 1.

6. The method of claim 5, wherein the pharmaceutical combination further comprises an antigen.

7. The method of claim 6, wherein the antigen is a peptide antigen.

8. The method of claim 6, wherein the antigen is a tumor-specific antigen.

9. The method of claim 5, wherein the immune system is stimulated for treatment of a cancer.

10. A vaccine comprising a pharmaceutical combination according to claim 1.

11. The vaccine according to claim 10, wherein the pharmaceutical combination further comprises an antigen.

12. The vaccine of claim 11, wherein the antigen is a peptide antigen.

13. The vaccine of claim 12, wherein the antigen is a tumor-specific antigen.

* * * * *